(12) United States Patent
Haick et al.

(10) Patent No.: US 12,196,699 B2
(45) Date of Patent: Jan. 14, 2025

(54) CHEMICALLY SENSITIVE SENSOR COMPRISING MICRO-BARRIER AND METHOD OF FABRICATION THEREOF

(71) Applicant: TECHNION RESEARCH & DEVELOPMENT FOUNDATION LIMITED, Haifa (IL)

(72) Inventors: Hossam Haick, Haifa (IL); Yana Milyutin, Nahariya (IL); Gidi Shani, Gesher Haziv (IL); Manal Abud Hawa, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 832 days.

(21) Appl. No.: 17/289,422

(22) PCT Filed: Oct. 30, 2019

(86) PCT No.: PCT/IL2019/051175
§ 371 (c)(1),
(2) Date: Apr. 28, 2021

(87) PCT Pub. No.: WO2020/089901
PCT Pub. Date: May 7, 2020

(65) Prior Publication Data
US 2021/0364461 A1 Nov. 25, 2021

Related U.S. Application Data

(60) Provisional application No. 62/753,948, filed on Nov. 1, 2018.

(51) Int. Cl.
*G01N 27/12* (2006.01)
*B82Y 35/00* (2011.01)
(Continued)

(52) U.S. Cl.
CPC ............ *G01N 27/127* (2013.01); *C01G 7/00* (2013.01); *G01N 33/0047* (2013.01);
(Continued)

(58) Field of Classification Search
None
See application file for complete search history.

(56) References Cited

U.S. PATENT DOCUMENTS 7,179,421 B1 2/2007 Ho
7,189,360 B1 3/2007 Ho
(Continued)

FOREIGN PATENT DOCUMENTS

CN 102326078 A 1/2012
JP 2005003593 A 1/2005

OTHER PUBLICATIONS

Adachi et al., (1995) Stripe Patterns Formed on a Glass Surface during Droplet Evaporation. Langmuir 11(4): 1057-1060 (4 pages).
(Continued)

*Primary Examiner* — J. Christopher Ball
(74) *Attorney, Agent, or Firm* — Roach Brown Mccarthy & Gruber, P.C.; Kevin D. McCarthy

(57) ABSTRACT

The present invention relates to a chemically sensitive sensor for detecting volatile organic compounds, the sensor comprising a substrate, an electrode array, a micro-barrier, and a sensing layer comprising a multiplicity of core-shell particles in close-packed orientation, the particles comprising a metal nanoparticle (MNP) core and an organic ligand shell, wherein the MNP core has a mean particle size below about 15 nm. The invention further provides a method for fabrication of the chemically sensitive sensor.

19 Claims, 16 Drawing Sheets

(51) Int. Cl.
| | |
|---|---|
| B82Y 40/00 | (2011.01) |
| C01G 7/00 | (2006.01) |
| G01N 33/00 | (2006.01) |
| G03F 7/038 | (2006.01) |
| G03F 7/20 | (2006.01) |
| G03F 7/32 | (2006.01) |

(52) U.S. Cl.
CPC .......... *G03F 7/0382* (2013.01); *G03F 7/2004* (2013.01); *G03F 7/32* (2013.01); *B82Y 35/00* (2013.01); *B82Y 40/00* (2013.01); *C01P 2004/04* (2013.01); *C01P 2004/64* (2013.01)

(56) References Cited

U.S. PATENT DOCUMENTS

| | | | |
|---|---|---|---|
| 7,922,939 | B2 | 4/2011 | Lewis et al. |
| 2010/0225337 | A1 | 9/2010 | Zamborini et al. |
| 2010/0273665 | A1 | 10/2010 | Haick et al. |
| 2014/0084390 | A1 | 3/2014 | Mayer et al. |
| 2014/0264642 | A1 | 9/2014 | Mayer et al. |
| 2018/0231486 | A1 | 8/2018 | Haick et al. |

OTHER PUBLICATIONS

Bekki et al., (1990) Solutal Marangoni effect: I. Pure interfacial transfer. Journal of Colloid and Interface Science 140(2): 492-506 (15 pages).

Brust et al., (1994) Synthesis of Thiol-derivatised Gold Nanoparticles in a Two-phase Liquid-Liquid System. J Chem Soc Chem Commun 2: 801-802 (3 pages).

Brust et al., (1995) Synthesis and reactions of functionalised gold nanoparticles. J Chem Soc Chem Commun 1995: 1655-1656 (2 pages).

Chow et al., (2009) Inkjet-printed gold nanoparticle chemiresistors: Influence of film morphology and ionic strength on the detection of organics dissolved in aqueous solution. Analytica Chimica Acta 632: 135-142 (8 pages).

Cui et al., (2012) Avoiding coffee ring structure based on hydrophobic silicon pillar arrays during single-drop evaporation. Soft Matter 8: 10448; (9 pages).

Deegan (2000) Pattern formation in drying drops. Phys Rev E 61(1): 475-485 (11 pages).

Deegan et al. (2000) Contact line deposits in an evaporating drop. Phys Rev E 62: 756-765 (10 pages).

Deegan et al., (1997) Capillary flow as the cause of ring stains from dried liquid drops. Nature 389: 827-829 (3 pages).

Dirk et al., (2009) Vapor Sensing Using Conjugated Molecule-Linked Au Nanoparticles in a Silica Matrix. Journal of Nanomaterials 2009: 481270; 10 pages.

Han and Lin (2012) Learning from "Coffee Rings": Ordered Structures Enabled by Controlled Evaporative Self-Assembly. Angewandte Chemie International EditionVolume 51(7): 1534-1546 (13 pages).

Hostetler et al., (1998) Alkanethiolate Gold Cluster Molecules with Core Diameters from 1.5 to 5.2 nm: Core and Monolayer Properties as a Function of Core Size. Langmuir 14: 17-30 (14 pages).

Hu and Larson (2005) Analysis of the Effects of Marangoni Stresses on the Microflow in an Evaporating Sessile Droplet. Langmuir 21(9): 3972-3980 (9 pages).

Hu and Larson (2006) Marangoni effect reverses coffee-ring depositions. J Phys Chem B 110(14): 7090-7094 (5 pages).

Kalinin et al., (2009) Contact line pinning by microfabricated patterns: effects of microscale topography. Langmuir. Author manuscript; available in PMC Mar. 1, 20105. Published in final edited form as: Langmuir. May 5, 2009; 25(9): 5391-5397 (21 pages).

Kim et al., (2006) Direct writing of silver conductive patterns: Improvement of film morphology and conductance by controlling solvent compositions. Applied Physics Letters 89: 264101; (3 pages).

Larson (2014) Transport and deposition patterns in drying sessile droplets. AIChE Journalvol.e 60(5): 1538-1571 (34 pages).

Li et al., (2016) Rate-dependent interface capture beyond the coffee-ring effect. Scientific Reports 6: 24628; (8 pages).

Neogi (1985) Tears-of-wine and related phenomena. Journal of Colloid and Interface Science 105(1): 94-101 (8 pages).

Park and Moon (2006) Control of Colloidal Particle Deposit Patterns within Picoliter Droplets Ejected by Ink-Jet Printing. Langmuir 22: 3506-3513 (8 pages).

Peng et al., (2009) Diagnosing lung cancer in exhaled breath using gold nanoparticles. Nat Nanotechnol 4(10): 669-673 (6 pages).

Pesach and Marmur (1987) Marangoni effects in the spreading of liquid mixtures on a solid. Langmuir 3(4): 519-524 (6 pages).

Popov (2004) Evaporative Deposition Patterns Revisited: Spatial Dimensions of the Deposit. arXiv:cond-mat/0408106v2 [cond-mat.soft]; (34 pages).

Scriven and Sterling (1960) The Marangoni Effects. Nature 187: 186-188 (3 pages).

Shafrin and Zisman (1960) Constitutive relations in the wetting of low energy surfaces and the theory of the retraction method of preparing monolayers. J Phys Chem 64(5): 519-524 (6 pages).

Shmuylovich et al., (2002) Surface Morphology of Drying Latex Films: Multiple Ring Formation. Langmuir 18(9): 3441-3445 (5 pages).

Soltman and Subramanian (2008) Inkjet-Printed Line Morphologies and Temperature Control of the Coffee Ring Effect. Langmuir 24(5): 2224-2231 (8 pages).

Stringer J and Derby B (2012) When the Drop Hits the Substrate. In: Inkjet Technology for Digital Fabrication. Edited by: Ian M. Hutchings, Graham D. Martin. John Wiley & Sons, Ltd. pp. 113-139 (27 pages).

Tekin et al., (2004) Ink-jet printing of polymers—from single dots to thin film libraries. J Mater Chem 14: 2627-2632 (6 pages).

Tekin et al., (2007) Inkjet Printing of Luminescent CdTe Nanocrystal-Polymer Composites. Adv Funct Mater 17: 23-28 (6 pages).

Wohltjen et al., (1985) A vapor-sensitive chemiresistor fabricated with planar microelectrodes and a Langmuir-Blodgett organic semiconductor film. IEEE Transactions on Electron Devices 32(7): 1170-1174 (5 pages).

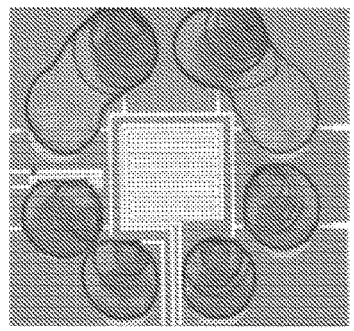
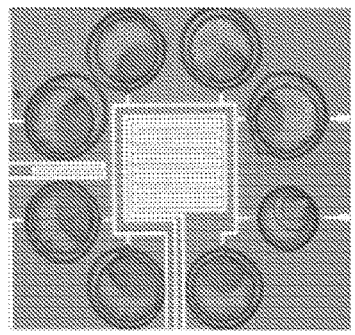
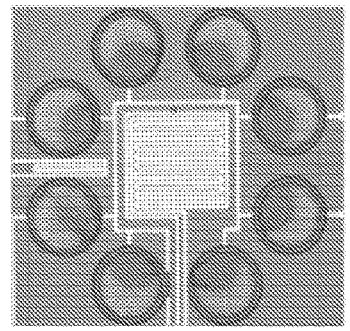
FIGURE 11A  FIGURE 11B  FIGURE 11C
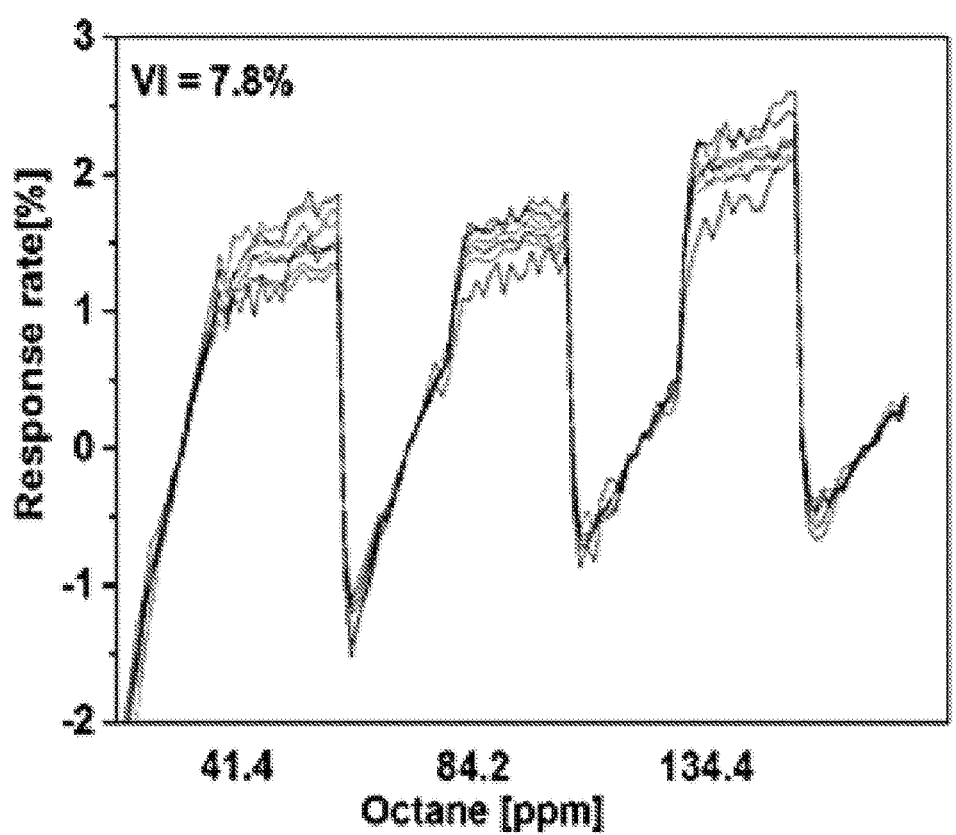
FIGURE 11D

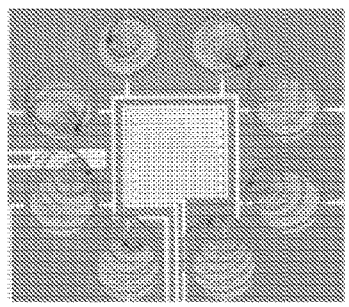 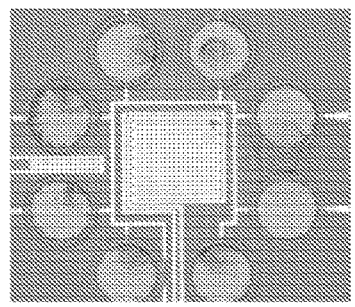 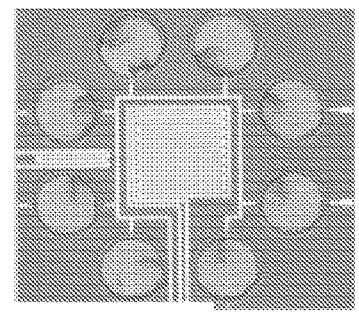
FIGURE 12A  FIGURE 12B  FIGURE 12C
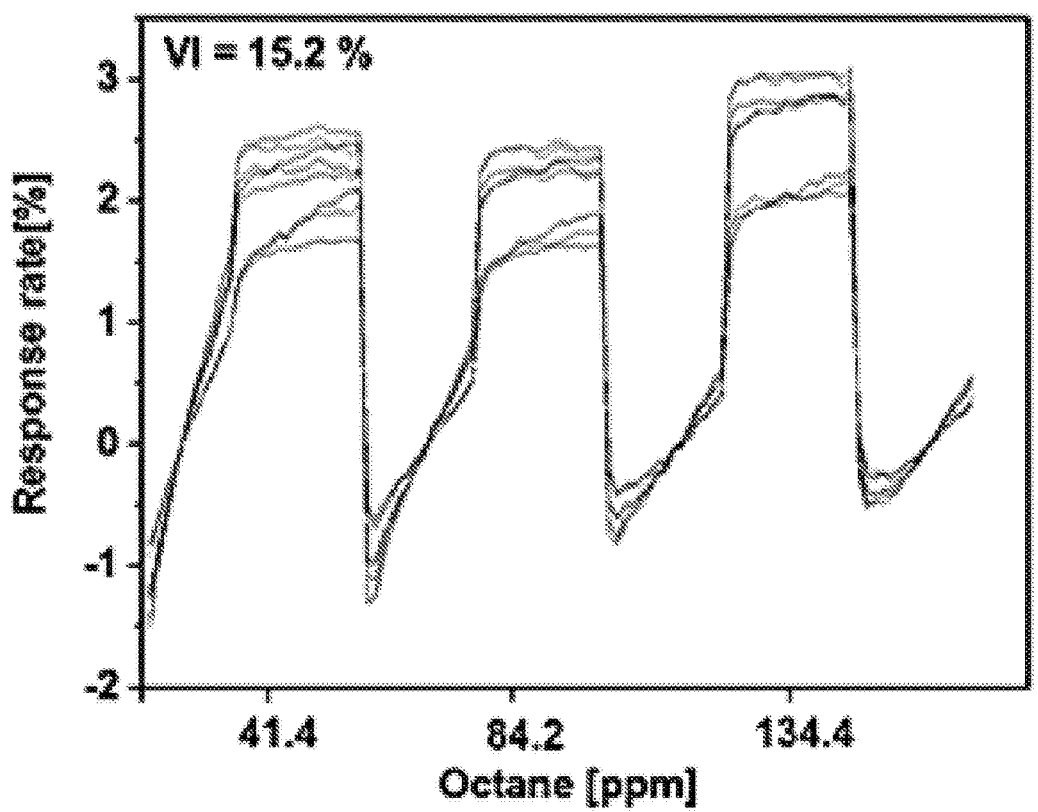
FIGURE 12D

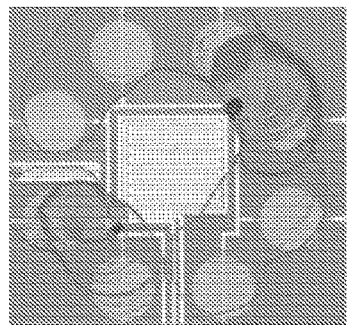 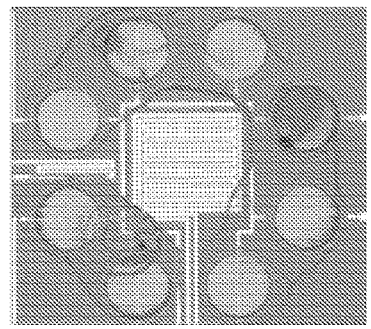 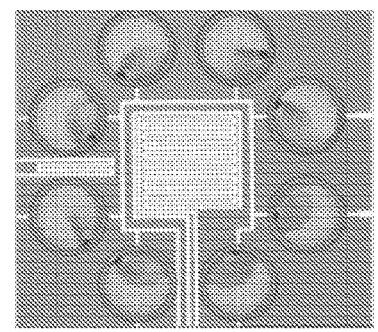
FIGURE 13A  FIGURE 13B  FIGURE 13C
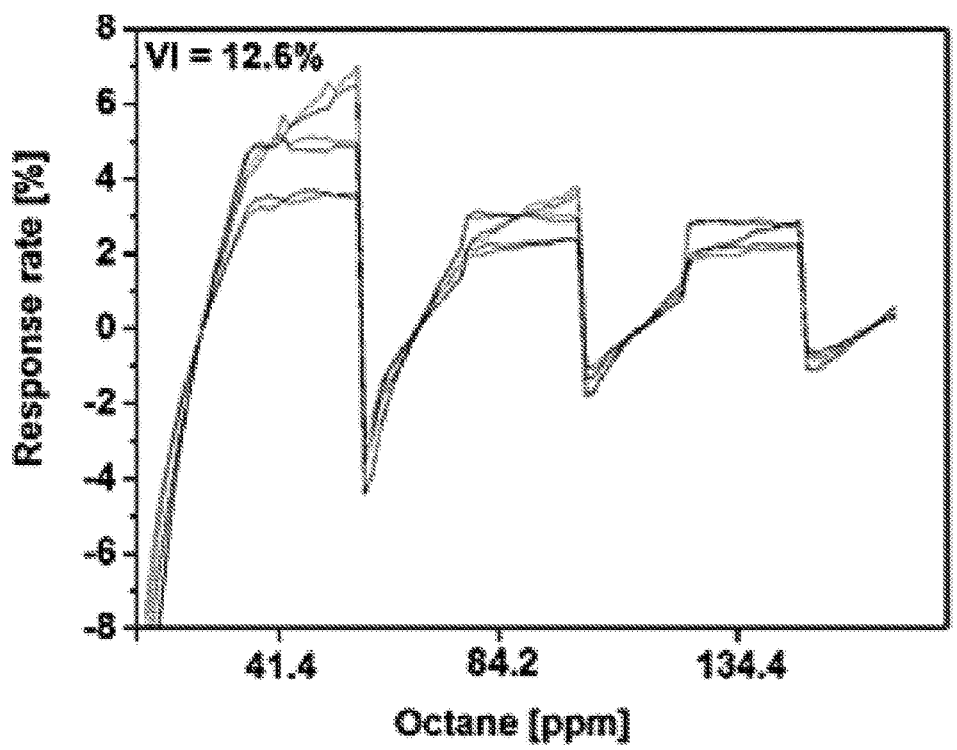
FIGURE 13D

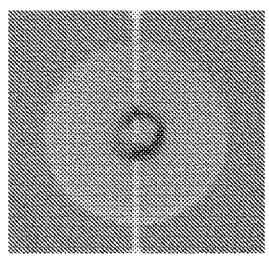 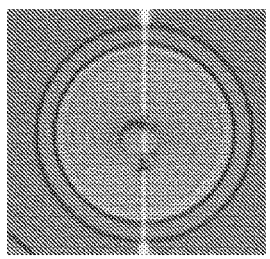 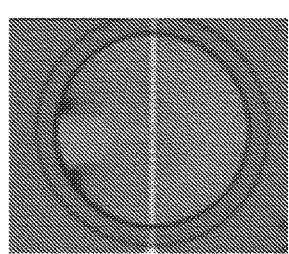 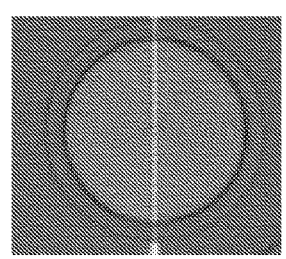
FIGURE 14A     FIGURE 14B     FIGURE 14C     FIGURE 14D
 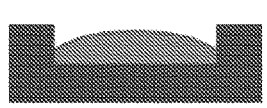 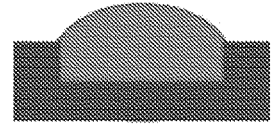 
FIGURE 15A     FIGURE 15B     FIGURE 15C     FIGURE 15D

CHEMICALLY SENSITIVE SENSOR COMPRISING MICRO-BARRIER AND METHOD OF FABRICATION THEREOF

FIELD OF THE INVENTION

The present invention relates to a chemically sensitive sensor for detecting volatile organic compounds, the sensor comprising a micro-barrier and a sensing layer based on organically capped metallic nanoparticles. The invention further provides a method for the fabrication of the chemically sensitive sensor.

BACKGROUND OF THE INVENTION

Chemically sensitive sensors can be employed in various applications, such as medical diagnosing, process-control and environmental-monitoring, due to their ability to detect various volatile organic compounds (VOCs). Chemically sensitive sensors are usually fabricated using conductive or semi-conductive materials, which are often based on metal nanoparticles (MNPs). Such sensors can contain a chemically sensitive semiconductor thin film formed by depositing a suspension comprising organically-modified MNPs and a suitable solvent onto planar microelectrodes. The electrodes are typically micro-fabricated in clean room facilities by photolithography, spattering or evaporation of noble metals, such as, for example, gold or platinum, or some transition metals, including, inter alia, titanium, and followed by lift-off process. In order to increase contact area between the chemically sensitive film and the electrodes, the electrodes can have an interdigitated design. The electrodes within the interdigitated array are typically separated by a few micrometer distances and are supported by an insulation layer, such as Si or $SiO_2$ (Wohltjen et al., IEEE Trans. Electron Devices., 1985, 32: 1170-1174).

U.S. Pat. No. 7,189,360 is directed to a circular chemiresistor for use in microchemical sensors. A pair of electrodes is fabricated on an electrically insulating substrate. The pattern of electrodes is arranged in a circle-filling geometry, such as a concentric, dual-track spiral design, or a circular interdigitated design. A drop of a chemically sensitive polymer (i.e., chemiresistive ink) is deposited on the insulating substrate on the electrodes, which spreads out into a thin, circular disk contacting the pair of electrodes. This circularly-shaped electrode geometry maximizes the contact area between the pair of electrodes and the polymer deposit, which provides a lower and more stable baseline resistance than with linear-trace designs.

Organically-modified MNPs suspension can be applied onto the electrodes by different techniques including, for example, drop-casting, layer-by-layer dipping, spin coating, and spraying. In recent years, an inkjet-printing technique was developed, which is more precise that the previously used methods. Typically, inkjet-printing technology is based on thermal or piezoelectric heads, which generate droplets in small (from pL to nL) volume of ink. When employed in the fabrication of chemically sensitive sensors, inkjet-printers use the MNPs suspension as the ink. Inkjet-printing is similar to drop casting, where the MNPs suspension is physically deposited onto the electrode spaces, while affording for significantly smaller and accurate drop size and precise ink deposition in predefined location on the substrate and/or the electrodes.

Drop-casting and inkjet printing techniques still suffer from film uniformity problems. In particular, following solvent evaporation, the organically-modified MNPs film adopts an irregular morphology, such as, for example, non-uniform thickness of the sensing layer, which has a strong influence on sensor's response. One particular type of irregular morphology of deposited particulate suspensions is termed "coffee ring", which can be observed as a narrow band of the particles deposited along the drop perimeter (also termed herein "contact line"), wherein the concentration of the particles in said band is significantly higher than in the central portion of the drop.

Morphological abnormalities of the deposited drop are believed to occur due to different attraction and repulsion forces acting on the particulate matter within the drop deposited onto a solid surface during solvent evaporation, said forces creating irregular movements of matter within the drying drop. In particular, the emergence of coffee rings is speculated to be the result of the capillary flow induced by the differential evaporation rates across the drop, wherein the liquid evaporating from the edge is replenished by the liquid from the interior of the drop. The outward flow in a drying drop of liquid is produced when the contact line is pinned to the underlying surface. The resulting outward flow can carry nearly all the dispersed material to the contact line and thus accounts for the strong perimeter concentration of the dried drops.

Additional effect acting on the drop during evaporation of the solvent is termed "Marangoni effect", which results from the concentration gradient throughout the drop or the evaporation-induced nonuniform cooling along the surface of the drying drop, which produces a temperature gradient. The concentration and/or temperature gradient leads to a surface-tension gradient along the droplet free surface. This surface-tension gradient, finally, induces a Marangoni (i.e., surface-tension-driven) flow that carries particles that are near the free liquid surface of the droplet inward toward the top of the droplet and then pushes them downward where they can either adsorb onto the substrate near the center of the droplet or be carried along the substrate to the edge, where they are recirculated along the free surface back toward the top of the droplet (Hu, H. and R. G. Larson, *Marangoni effect reverses coffee-ring depositions*. Journal of Physical Chemistry B, 2006. 110(14): p. 7090-7094). The surface tension gradient therefore causes circulation of matter in opposite direction to the formed concentration gradient and as such decreases coffee-ring deposition. Morphological non-uniformity of the deposited film occurs despite strict control over drop casting volume, ambient temperature, relative humidity, surrounding gas atmosphere and other external conditions.

Considerable efforts have been made to eliminate or at least decrease the coffee ring and Marangoni effect during deposition of various solutions and suspensions. Deegan et al. (Phys. Rev. E., 2000, 62, 756-765) demonstrated that the coffee ring formation can be suppressed by depositing the droplet on smooth Teflon surface to eliminate contact line pinning. As the evaporation proceeded, the droplet contracted and no ring has appeared. Additionally, uniformity of the deposit was increased by reducing the proportion of evaporation from the perimeter of the drop by covering the drop with a lid that had only a small hole over the center of the drop through which the vapor could escape.

Use of a mixture of solvents, one with high-boiling point and the other with low-boiling point was shown to produce uniform films of high molar mass polystyrene (J. Mater. Chem., 2004, 14, 2627-2632). This method has been further applied in the inkjet deposition of CdTe nanocrystals, silica particles and silver nanoparticles (Adv. Funct. Mater., 2007, 17, 23-28; Langmuir, 2006, 22, 3506-3513; App. Phsy. Lett., 2006, 89, 264101). Chow et al. (Analytica Chimica Acta, 2009, 632, 135-142) demonstrated that the uniformity of gold nanoparticles (NPs) films could be improved if the nanoparticles ink was deposited from a two-solvent system comprising N-methyl-2-pyrrolidone and water.

However, addition of a secondary solvent to the MNPs suspension during fabrication of a chemically sensitive sensor can sometimes be undesired or even impossible. In general, multi-substance solvents are considered highly cumbersome and are impractical for industrial application. The type of the substrate is typically dictated by the intended sensor application and cannot be easily changed. Reducing solvent evaporation rate is not economically viable and complicates sensor fabrication process.

There remains, therefore, an unmet need for a simple and universal solution, which would allow uniform deposition of organically-modified MNPs suspensions, thereby providing highly reliable and functionally reproducible VOCs sensors. Preferably, such solution should also increase reproducibility of sensor fabrication and allow optimization of the manufacturing process.

SUMMARY OF THE INVENTION

The present invention provides a chemically sensitive sensor for detecting VOCs. The sensor comprises a substrate, an electrode array, a micro-barrier and a sensing layer. The sensing layer is formed of a core-shell material comprising metal nanoparticle cores capped by a shell of organic ligands. The micro-barrier surrounds the electrode array and the sensing layer, therefore defining the shape and the area of said layer. Further provided is a method of fabrication of said chemically sensitive sensor, wherein the addition of the micro-barrier can be implemented by a simple and readily-available process, such as for example, photolithography.

The invention is based in part on the unexpected finding that chemically sensitive sensors comprising a MNPs-based sensing layer, which is confined by a micro-barrier, provide highly uniform responses when exposed to VOCs. It was not previously realized that a physical micro-barrier surrounding the deposited nanoparticles' dispersion can decrease the extent of coffee ring formation, hinder evolution of the overall morphological irregularities of the sensing layer and increase functional reproducibility of the sensors. Increased reproducibility of the sensor response can further be induced by fine-tuning of the physical parameters and the material of the micro-barrier. In particular, the inventors have surprisingly found that using hydrophobic material for the formation of the micro-barrier significantly enhances sensor response reproducibility as compared to the sensors which do not include a micro-barrier and sensors with micro-barriers made of a hydrophilic material. Furthermore, the volume of the deposited MNPs suspension can be adjusted such that the drop height is aligned with the micro-barrier height, to further control uniformity of the sensing layer. Additionally, a combination of the hydrophobic micro-barrier with a hydrophilic substrate, which underlays the electrode array, provided the lowest variance of the sensors' responses.

Thus, according to one aspect, the present invention provides a chemically sensitive sensor for detecting volatile organic compounds (VOCs), the sensor comprising: a substantially planar substrate having a top surface and a bottom surface, the substrate made of an electrically insulating material; an electrode array being disposed on the top surface of said substrate; a micro-barrier comprising an inner face and an outer face and being disposed on the top surface of the substrate and surrounding the electrode array; and a sensing layer comprising a multiplicity of core-shell particles in close-packed orientation, the particles comprising a metal nanoparticle (MNP) core and an organic ligand shell, wherein the MNP core has a mean particle size below about 15 nm, the sensing layer is in electric contact with said electrode array, and the shape of said sensing layer is confined by the micro-barrier.

According to some embodiments, said micro-barrier is made of a hydrophobic material. According to additional embodiments, the sensing layer is hydrophobic.

The micro-barrier can have s cross-sectional shape selected from the group consisting of circular, oval, square, rectangular, triangular, hexagonal, and polygon shape. Each possibility represents a separate embodiment of the invention.

According to some embodiments, said micro-barrier has a height ranging from about 1 µm to about 20 µm. According to further embodiments, the micro-barrier has a height ranging from about 2 µm to about 5 µm. According to additional embodiments, said micro-barrier has a thickness ranging from about 10 µm to about 500 µm. According to some embodiments, the micro-barrier has an inner perimeter ranging from about 0.2 mm to about 15 mm. According to further embodiments, said micro-barrier has a circular cross-sectional shape with an inner diameter ranging from about 0.2 mm to about 5 mm. According to yet further embodiments, the inner face of the micro-barrier is substantially orthogonal to the top surface of the substrate. According to still further embodiments, said inner face is substantially smooth.

According to some embodiments, the micro-barrier is made of an electrically insulating material. According to additional embodiments, said micro-barrier is made of an epoxy-based photoresist. According to some exemplary embodiments, the epoxy-based photoresist is SU-8.

According to some embodiments, said MNP core has a mean particle size ranging from about 1.5 nm to about 5 nm. According to additional embodiments, the organic ligand shell has a thickness ranging from about 1.2 nm to about 7 nm. Said core-shell particles can be arranged in a film configuration.

The MNP core can comprise a metal selected from the group consisting of Au, Pt, Ag, Ni, Co, Pd, Cu, Al, Zn, Fe, and combinations thereof. According to some embodiments, said MNP core comprises a metal alloy selected from the group consisting of Au/Pt, Au/Ag, Au/Cu, Au/Ag/Cu, Au/Pd, Au/Ag/Cu/Pd, Pt/Rh, Ni/Co, and Pt/Ni/Fe. Each possibility represents a separate embodiment of the invention. According to some exemplary embodiments, the MNP core comprises Au.

The organic ligand can be selected from the group consisting of alkylthiols, arylthiols, alkylarylthiols, alkylthiolates, ω-functionalized alkanethiolates, arenethiolates, (γ-mercaptopropyl)tri-methyloxysilane, dialkyl disulfides and combinations and derivatives thereof. According to some embodiments, the ligand is selected from the group consisting of dodecanethiol, 2-ethylhexanethiol, decanethiol, hexanethiol, dibutyl disulfide, 4-tert methylbenzenethiol, 1-heptanethiol, butanethiol, benzylmercaptan, 3-ethoxytiophenol, tert-dodecanethiol and combinations thereof. According to some exemplary embodiments, the ligand is selected from dodecanethiol and 2-ethylhexanethiol. Each possibility represents a separate embodiment of the invention.

According to some currently preferred embodiments, the sensing layer has a substantially uniform thickness throughout its entire area.

According to certain embodiments, said sensing layer is essentially devoid of a polymer.

According to some embodiments, the substrate is made of the electrically insulating material selected from the group consisting of silicon, silicon dioxide, quartz, glass, ceramic, plastic, Teflon, Kapton, and combinations thereof. Each possibility represents a separate embodiment of the invention. According to additional embodiments, said substrate is made of the electrically insulating material which is hydrophilic.

According to some embodiments, the electrode array comprises a plurality of interdigitated electrodes. According to further embodiments, the electrodes are made of a material selected from the group consisting of Au, Pt, Ti, Cu, Ag, Pd, Ni, Al, and alloys and combinations thereof. Each possibility represents a separate embodiment of the invention.

According to some embodiments, the chemically sensitive sensor comprises a plurality of electrode arrays, micro-barriers and sensing layers disposed on the top surface of the substrate.

According to another aspect, the present invention provides a method for fabricating a chemically sensitive sensor for detecting volatile VOCs, the method comprising the steps of:
i. providing a substantially planar substrate having a top surface and a bottom surface, the substrate being made of an electrically insulating material;
ii. forming an electrode array on the top surface of the substrate;
iii. forming a micro-barrier on the top surface of the substrate, wherein the micro-barrier surrounds the electrode array; and
iv. forming a sensing layer comprising a multiplicity of core-shell particles in close-packed orientation, the particles comprising a metal nanoparticle (MNP) core and an organic ligand shell, wherein the MNP core has a mean particle size below about 15 nm, the sensing layer is in electric contact with the electrode array, and the shape of the sensing layer is confined by said micro-barrier.

According to some embodiments, the micro-barrier is made of a hydrophobic material.

According to some embodiments, the step of forming the micro barrier is performed by a photolithography process comprising applying a negative photoresist to the substrate and the electrode array, disposing a mask with a predefined pattern on the negative photoresist, exposing the negative photoresist to ultraviolet (UV) irradiation, and developing the remaining negative photoresist. According to further embodiments, the negative photoresist comprises an epoxy-based photoresist. According to yet further embodiments, the negative photoresist is applied to the substrate and the electrode array by spinning at a rate ranging from about 200 rpm to about 5000 rpm. According to still further embodiments, the spinning is performed for about 5 to about 120 seconds. According to yet further embodiments, the mask has a ring-shaped opening in a shape selected from the group consisting of circular, oval, square, rectangular, triangular, hexagonal, and polygon ring shape. Each possibility represents a separate embodiment of the invention. According to a certain embodiment, the photolithography process does not include a step of photoresist lift-off.

According to some embodiments, the step of forming a sensing layer comprises applying a dispersion comprising the core-shell particles and a solvent onto the top surface of the substrate and/or the electrode array within the micro-barrier. According to further embodiments, the dispersion is hydrophobic. The dispersion can be applied by a process selected from inkjet-printing and drop-casting. Each possibility represents a separate embodiment of the invention. According to certain embodiments, the dispersion is applied by inkjet-printing. According to some embodiments, the dispersion is applied in a volume ranging from about 5 nL to about 150 nL. According to further embodiments, said dispersion is applied in a volume which forms a drop, having essentially same height as the height of the micro-barrier.

According to some embodiments, the MNP core of the core-shell particles comprises a metal selected from the group consisting of Au, Pt, Ag, Ni, Co, Pd, Cu, Al, Zn, Fe, and combinations thereof. According to further embodiments, the MNP core comprises a metal alloy selected from the group consisting of Au/Pt, Au/Ag, Au/Cu, Au/Ag/Cu, Au/Pd, Au/Ag/Cu/Pd, Pt/Rh, Ni/Co, and Pt/Ni/Fe. Each possibility represents a separate embodiment of the invention. According to some exemplary embodiments, said MNP core comprises Au.

According to some embodiments, the organic ligand of the core-shell particles is selected from the group consisting of alkylthiols, arylthiols, alkylarylthiols, alkylthiolates, ω-functionalized alkanethiolates, arenethiolates, (γ-mercaptopropyl)tri-methyloxysilane, dialkyl disulfides and combinations and derivatives thereof. According to further embodiments, the organic ligand is selected from the group consisting of dodecanethiol, 2-ethylhexanethiol, decanethiol, hexanethiol, dibutyl disulfide, 4-tert methylbenzenethiol, 1-heptanethiol, butanethiol, benzylmercaptan, 3-ethoxytiophenol, tert-dodecanethiol and combinations thereof. According to some exemplary embodiments, the organic ligand is selected dodecanethiol and 2-ethylhexanethiol. Each possibility represents a separate embodiment of the invention.

The solvent of the dispersion can be selected from the group consisting of toluene, 2-pentatone, ethanol and combinations thereof. Each possibility represents a separate embodiment of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

Some of the embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

(FIG. 8A) shows an optical-microscopy image of contact angle on SU-8 surface, (FIG. 8B) shows an optical-microscopy image of contact angle on treated oxygen-plasma SU-8 surface, and (FIG. 8C) shows an optical-microscopy image of contact angle on $SiO_2$ surface.

(FIG. 9A) shows a SEM image of $SiO_2$ micro-barrier at a magnification of 10k, (FIG. 9B) shows a SEM image of a SU-8 micro-barrier at a magnification of 10k, (FIG. 9C) shows a SEM image of the $SiO_2$ micro-barrier at a magnification of 1k, and (FIG. 9D) shows a SEM image of the SU-8 micro-barrier at a magnification of 1k.

FIG. 11A: Light-microscopy image of a sensor comprising 8 electrode arrays and a sensing layer prepared by deposition of 40 nL of 2-ethylhexaethiol-capped Au NPs dispersion.

FIG. 11B: Light-microscopy image of a sensor comprising 8 electrode arrays and a sensing layer prepared by deposition of 40 nL of 2-ethylhexaethiol-capped Au NPs dispersion, wherein the sensing layer is confined by $SiO_2$ micro-barrier.

FIG. 11C: Light-microscopy image of a sensor comprising 8 electrode arrays and a sensing layer prepared by deposition of 40 nL of 2-ethylhexaethiol-capped Au NPs dispersion, wherein the sensing layer is confined by SU-8 micro-barrier.

FIG. 11D: Response rate of a sensor to the exposure of different concentrations of n-octanol, wherein the sensor comprising 8 electrode arrays and a sensing layer prepared by deposition of 40 nL of 2-ethylhexaethiol-capped Au NPs dispersion.

FIG. 12A: Light-microscopy image of a sensor comprising 8 electrode arrays and a sensing layer prepared by deposition of 20 nL of dodecanethiol-capped Au NPs dispersion.

FIG. 12B: Light-microscopy image of a sensor comprising 8 electrode arrays and a sensing layer prepared by deposition of 20 nL of dodecanethiol-capped Au NPs dispersion, wherein the sensing layer is confined by $SiO_2$ micro-barrier.

FIG. 12C: Light-microscopy image of a sensor comprising 8 electrode arrays and a sensing layer prepared by deposition of 20 nL of dodecanethiol-capped Au NPs dispersion, wherein the sensing layer is confined by SU-8 micro-barrier.

FIG. 12D: Response rate of a sensor to the exposure of different concentrations of n-octanol, wherein the sensor comprising 8 electrode arrays and a sensing layer prepared by deposition of 20 nL of dodecanethiol-capped Au NPs dispersion.

FIG. 13A: Light-microscopy image of a sensor comprising 8 electrode arrays and a sensing layer prepared by deposition of 40 nL of dodecanethiol-capped Au NPs dispersion.

FIG. 13B: Light-microscopy image of a sensor comprising 8 electrode arrays and a sensing layer prepared by deposition of 40 nL of dodecanethiol-capped Au NPs dispersion, wherein the sensing layer is confined by $SiO_2$ micro-barrier.

FIG. 13C: Light-microscopy image of a sensor comprising 8 electrode arrays and a sensing layer prepared by deposition of 40 nL of dodecanethiol-capped Au NPs dispersion, wherein the sensing layer is confined by SU-8 micro-barrier.

FIG. 13D: Response rate of a sensor to the exposure of different concentrations of n-octanol, wherein the sensor comprising 8 electrode arrays and a sensing layer prepared by deposition of 40 nL of dodecanethiol-capped Au NPs dispersion.

FIG. 14A: Light-microscopy image of a sensor comprising one electrode array and a sensing layer prepared by deposition of 15 nL of dodecanethiol-capped Au NPs dispersion.

FIG. 14B: Light-microscopy image of a sensor comprising one electrode array and a sensing layer prepared by deposition of 10 nL of dodecanethiol-capped Au NPs dispersion, wherein the sensing layer is confined by a micro-barrier.

FIG. 14C: Light-microscopy image of a sensor comprising one electrode array and a sensing layer prepared by deposition of 22 nL of dodecanethiol-capped Au NPs dispersion, wherein the sensing layer is confined by a micro-barrier.

FIG. 14D: Light-microscopy image of a sensor comprising one electrode array and a sensing layer prepared by deposition of 20 nL of dodecanethiol-capped Au NPs dispersion, wherein the sensing layer is confined by a micro-barrier.

FIG. 15A: Schematic representation of the cross-section of a drop formed on the substrate by depositing 15 nL of dodecanethiol-capped Au NPs dispersion.

FIG. 15B: Schematic representation of the cross-section of a drop formed on the substrate by depositing 10 nL of dodecanethiol-capped Au NPs dispersion, the drop being confined by a micro-barrier.

FIG. 15C: Schematic representation of the cross-section of a drop formed on the substrate by depositing 22 nL of dodecanethiol-capped Au NPs dispersion, the drop being confined by a micro-barrier.

FIG. 15D: Schematic representation of the cross-section of a drop formed on the substrate by depositing 20 nL of dodecanethiol-capped Au NPs dispersion, the drop being confined by a micro-barrier.

DETAILED DESCRIPTION OF THE INVENTION

Figure 1A:
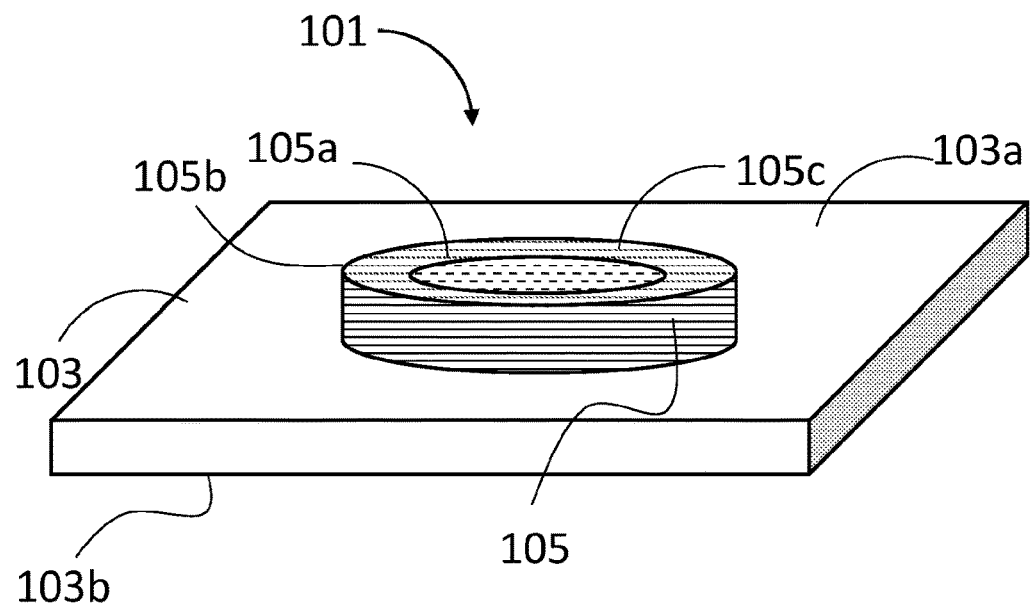
FIG. 1A: Schematic side view representation of a sensor comprising a circular micro-barrier, prior to the formation of the sensing layer.

The present invention provides a chemically sensitive sensor for detecting volatile organic compounds (VOCs), the sensor comprising a substrate, an electrode array disposed on said substrate, a micro-barrier, disposed on the substrate and surrounding the electrode array, and a MNPs-based sensing layer being in electric contact with the electrode array, wherein the shape of the sensing layer is confined by the micro-barrier. Further provided is a method for fabricating a chemically sensitive sensor for detecting volatile VOCs. The chemically sensitive sensors according to the principles of the present invention are highly reliable and functionally reproducible. The structure of the sensors and the method of their preparation increase reproducibility of sensor fabrication and allow optimization of the manufacturing process, thereby promoting its automation and simplifying of quality control.

The sensor and method of the present invention are particularly suitable for use with core-shell particles comprising metal nanoparticle cores having a mean particle size below about 15 nm and a shell of organic ligands. As explained hereinabove, sensing layers comprising such particles are prone to exhibiting non-uniform morphologies, when manufactured by drop casting or inkjet printing. It was found by the inventors of the present invention that the addition of a physical barrier not only prevents spreading of the deposited MNPs dispersion beyond the desired area, but also allows formation of a more uniform sensing layer. The effect of the micro-barrier addition is surprising as it enhances pinning of drops to the substrate surfaces, which is known to induce the evolution of coffee ring formation. A study exploring contact line pinning of water and glycerol drops disposed on hydrophilic silicon wafer surfaces and confined by micropatterned photoresist polymer rings of varying cross-sectional size and shape showed that microscale circular polymer rings enhance pinning of drops to surfaces (Kalinin, Y. V., Berejnov, V., & Thorne, R. E. (2009). Contact Line Pinning by Microfabricated Patterns. Effects of Microscale Topography. *Langmuir: The ACS Journal of Surfaces and Colloids*, 25(9), 5391-5397).

It was further found that using hydrophobic micro-barrier provided lower thickness variance throughout the sensing layer as compared to the use of a hydrophilic micro-barrier. The MNP-s dispersion which was applied onto the substrate surrounded by the micro-barrier was also hydrophobic. Without wishing to being bound by theory or mechanism of action, it is believed that the micro-barrier prevents formation of a high contact angle between the substrate surface and the applied MNPs-based dispersion, thereby allowing more even evaporation of the dispersion solvent, which decreases concentration and temperature gradients throughout the drying drop. It is therefore assumed that the Marangoni flow within such drying drop surrounded by a micro-barrier is reduced, thereby restricting particle motion within the drop. However, as mentioned hereinabove, suppressing Marangoni effect can induce coffee ring deposition. Furthermore, combination of a hydrophobic micro-barrier and a hydrophobic drop should theoretically result in a high wetting of the micro-barrier surface, thereby providing a less even drop surface. Formation of a more homogeneous sensing layer and enhanced functional reproducibility of the drop-casted or printed sensors, which was achieved by the addition of a micro-barrier, was therefore completely unforeseen in view of the combination of factors which are supposed to increase the extent of the coffee ring formation and affect the Marangoni flow. It should be noted that the micro-barrier can be added to any substrate suitable for use in sensor fabrication. The positive effect of the addition of the hydrophobic micro-barrier is believed to be more pronounced when said hydrophobic micro-barrier is used in combination with a substrate having a hydrophilic surface, such as, for example, silicon dioxide.

Increased reproducibility of the sensor response can further be induced by fine-tuning of the thickness of the sensing layer and the volume of the deposited MNPs-based dispersion. In particular, the volume of the deposited MNPs suspension or dispersion can be adjusted such that the drop height is aligned with the micro-barrier height, to further control uniformity of the solvent evaporation and reduce thickness variance throughout the sensing layer. Additional improvement of the sensors' structural and functional reproducibility can be attained by ensuring that the micro-barrier is substantially orthogonal to the top surface of the substrate and/or by reducing the surface roughness of the micro-barrier inner walls.

Thus, according to one aspect, the present invention provides a chemically sensitive sensor for detecting VOCs, the sensor comprising a substrate having a top surface and a bottom surface, the substrate made of an electrically insulating material; an electrode array being disposed on the top surface of the substrate; a micro-barrier comprising an inner face and an outer face and being disposed on the top surface of the substrate and surrounding the electrode array; and a sensing layer comprising a multiplicity of core-shell particles, the particles comprising a metal nanoparticle (MNP) core and an organic ligand shell, wherein the MNP core has a mean particle size below about 15 nm, the sensing layer is in electric contact with the electrode array, and the shape of the sensing layer is confined by the micro-barrier.

According to another aspect, there is provided a method for fabricating a chemically sensitive sensor for detecting volatile VOCs, the method comprising the steps of: i. providing a substrate having a top surface and a bottom surface, the substrate being made of an electrically insulating material; ii. forming an electrode array on the top surface of the substrate; iii. forming a micro-barrier on the top surface of the substrate, wherein the micro-barrier surrounds the electrode array; and iv. Forming a sensing layer comprising a multiplicity of core-shell particles, the particles comprising a metal nanoparticle (MNP) core and an organic ligand shell, wherein the MNP core has a mean particle size below about 15 nm, the sensing layer is in electric contact with the electrode array, and the shape of the sensing layer is confined by the micro-barrier.

The term "multiplicity of core-shell particles", as used herein, refers to two or more core-shell particles, such as, e.g., 50, 100, 500, 1000, 5000, or 10000 particles.

The term "volatile organic compound (VOC)", as used herein, is intended to encompass organic compounds having high or low volatility (such as semi-volatile organic compounds), inorganic volatile compounds (VCs), other solvents, volatile toxic chemicals, and volatile explosives.

Substrate

The substrate of the sensor is configured to support the electrode array, the micro-barrier and the sensing layer. The substrate can by any substrate suitable for use in the fabrication of VOCs sensors. In some embodiments, the substrate is an integral part of a printed circuit or a printed electronics component. Non-limiting examples of the suitable substrate materials include silicon, silicon dioxide, quartz, glass, ceramics, plastic, Teflon, Kapton, and combinations thereof.

In some currently preferred embodiments, the substrate is made of a hydrophilic material or has a hydrophobic surface. In certain embodiments, the substrate is made of silicon. In additional embodiments, the substrate is made of silicon coated by a layer of native or intentionally formed silicon oxide. In certain such embodiments, the top layer of the substrate includes silicon dioxide.

The term "hydrophilic", as used herein, refers in some embodiments to a material or object, having a water contact angle below 90°. In further embodiments, the term "hydrophilic" refers to a material or object, having a water contact angle below 80°, below 70° or below 60°. Each possibility represents a separate embodiment of the invention.

According to some embodiments, the substrate is substantially planar. The term "substantially planar", as used herein, refers in some embodiments to components that have their main extension in one plane in contrast to being shaped. In a certain embodiment, a substantially planar substrate has a constant thickness throughout the longest dimension thereof. This does not exclude a general curvature of the substrate. According to some embodiments, the substrate has a thickness of at least about 0.1 µm. According to further embodiments, the substrate has a thickness of at least about 0.5 µm or at least about 1 µm.

The substrate can further include electric circuit configured to control the sensor or to operatively connect the sensor to a measuring device and/or computing system, wherein the connection is implemented as known in the art, e.g., via suitable electric wires or wirelessly. The substrate can further include an additional type of sensor, such as, but not limited to, resistor, capacitor, quartz crystal microbalance, bulk acoustic wave (BAW) and surface acoustic wave (SAW) resonator, electrochemical cell, surface plasmon resonance (SPR), and optical spectroscope. The additional sensor can be configured for the detection of at least one of temperature, humidity, and pressure.

Electrode Array

The electrode array can include a pair of electrodes (a positive electrode and a negative electrode) or a plurality of said pairs of electrodes. The term "plurality", as used herein, means two or more. The positive and the negative electrode can be separated by a gap ranging from about 0.2 mm to about 5 mm. In further embodiments, the gap ranges from about 0.5 mm to about 2.5 mm.

The electrode array can further comprise patterned electrodes, for example, interdigitated electrodes. In some embodiments, the electrode array includes a plurality of sets of interdigitated electrodes. In some embodiments, the substrate includes a plurality of electrode arrays. The interdigitated electrodes can have any shape known in the art, such as, but not limited to circular, square, rectangular, triangular, or any other particular shape and geometry. Each possibility represents a separate embodiment of the invention. In some currently preferred embodiments, the electrode array comprises interdigitated circular electrodes. In some embodiments, the interdigitated electrodes have an outer diameter ranging from about 0.2 mm to about 5 mm. In further embodiments, the interdigitated electrodes have an outer diameter ranging from about 0.5 mm to about 2.5 mm. The gaps between each two electrodes in the interdigitated electrode array can range from about 2 µm to about 50 µm. In some embodiments, the gaps range from about 5 µm to about 20 µm. The thickness of the electrodes in the interdigitated electrode array can range from about 2 µm to about 50 µm. In some embodiments, the thickness ranges from about 5 µm to about 20 µm.

Alternatively, the electrode array may include a source and a drain electrode separated from one another by a source-drain gap. The electrode array may further comprise a gate electrode wherein the electric signal may be indicative of a certain property of the sensing layer under the influence of a gate voltage.

The electrode array can comprise any metal having high electric conductivity. Non-limiting examples of metals suitable for use in the electrode array of the VOCs sensor of the present invention include Au, Ti, Cu, Ag, Pd, Pt, Ni, Al, and combinations thereof. In some exemplary embodiments, the electrode array comprises Pt electrodes.

In some embodiments, the sensing layer is disposed on top of the electrode array, for example, wherein said electrode array comprises interdigitated electrodes. In some embodiments, the sensing layer is disposed between the electrodes of the electrode array, for example wherein the electrode array includes a pair of electrodes.

Micro-Barrier

The term "micro-barrier", as used herein, refers in some embodiments to a raised frame structure having any cross-sectional shape or geometry, disposed on the top surface of the substrate and surrounding the electrode array. The term "micro-barrier" is meant to encompass a frame structure which has a longest dimension in a micrometer or a millimeter range, i.e., ranging from about 1 µm to about 1000 mm, for example, from about 10 µm or about 50 µm or about 100 µm to about 1 mm or about 10 mm or about 50 mm or about 100 mm.

In some embodiments, the micro-barrier has an internal face and an external face. The distance between the external face and the internal face is defined as micro-barrier thickness. The extent to which the micro-barrier is raised above the top surface of the substrate is defined as micro-barrier height. The micro-barrier defines the shape and/or area of the sensing layer. The term "defines the shape and/or area of the sensing layer", as used herein, refers in some embodiments to the confinement of the sensing layer by the micro-barrier, such that the area of the sensing area cannot be larger than the cross-sectional area of the micro-barrier. In some embodiments, the perimeter of the inner face of the micro-barrier defines the shape and/or area of the sensing layer.

According to some embodiments, the shape of the electrode array dictates the shape and/or the cross-sectional area of the micro-barrier. The micro-barrier can have a cross-sectional shape selected from circular, oval, square, rectangular, triangular, hexagonal, polygonal, or in any other particular shape or geometry. Each possibility represents a separate embodiment of the invention. In certain embodiments, the micro-barrier has a circular cross-section.

In some embodiments, micro-barrier has an inner perimeter ranging from about 0.5 mm to about 15 mm. In further embodiments, micro-barrier has an inner perimeter ranging from about 1 mm to about 10 mm. The term "inner perimeter", as used herein, refers in some embodiments to the perimeter of the inner face of the micro-barrier.

In certain embodiments, the micro-barrier has a circular cross-sectional shape with an inner diameter ranging from about 0.2 mm to about 5 mm. In certain embodiments, the micro-barrier has a circular cross-sectional shape with an inner diameter ranging from about 0.5 mm to about 2.5 mm. In some exemplary embodiments, the micro-barrier has a circular cross-sectional shape with an inner diameter of about 0.1 mm. The term "inner diameter", as used herein, refers in some embodiments to the diameter of the inner face of the micro-barrier, when the micro-barrier has a circular cross-section.

The height of the micro-barrier can be chosen to prevent spreading of the sensing layer beyond the perimeter of the micro-barrier and/or the outer perimeter of the electrode-array. For example, if the sensing area is formed by drop casting a dispersion comprising core-shell particles, the micro-barrier can prevent spillover of said dispersion when applied onto the substrate. Furthermore, the height of the micro-barrier can be adjusted to be level with the deposited dispersion drop. According to some embodiments, the micro-barrier has a height ranging from about 0.5 µm to about 50 µm. According to further embodiments, the micro-barrier has a height ranging from about 0.5 µm to about 30 µm. According to yet further embodiments, the micro-barrier has a height ranging from about 1 µm to about 20 µm. According to still further embodiments, the micro-barrier has a height ranging from about 1 µm to about 10 µm. In yet further embodiments, the height of the micro-barrier ranges from about 2 µm to about 5 µm. In certain embodiments, the height of the micro-barrier is about 2.5 µm.

According to some embodiments, the inner face of the micro-barrier is substantially orthogonal to the top surface of the substrate. In further embodiments, the inner face of the micro-barrier is substantially orthogonal to the top surface of the substrate throughout the entire height of the micro-barrier. In additional embodiments, the outer face of the micro-barrier is substantially orthogonal to the top surface of the substrate. The term "orthogonal", as used herein, refers in some embodiments to an angle between the micro-barrier inner or outer face and the top surface of the substrate, which ranges from about 85° to about 95°. Preferably, the thickness of the micro-barrier (i.e., the distance between the inner face and the outer face) is essentially constant throughout the entire perimeter and/or height thereof. According to some embodiments, the thickness of the micro-barrier ranges from about 20 to about 500 µm. According to some embodiments, the thickness of the micro-barrier ranges from about 50 to about 200 µm. In some exemplary embodiments, the thickness of the micro-barrier is about 100 µm.

According to some currently preferred embodiments, the inner face of the micro-barrier is substantially smooth. The term "substantially smooth", as used herein, refers in some embodiments, to a surface having a roughness of less than about 0.5 nm. The roughness of the micro-barrier inner surface can be evaluated by investigating SEM images or by Atomic Force Microscopy (AFM) measurements.

According to some currently preferred embodiments, the micro-barrier is made of a hydrophobic material. The term "hydrophobic", as used herein, refers in some embodiments to a material or object, having a water contact angle above 90°. In further embodiments, the term "hydrophobic" refers to a material or object, having a water contact angle above 100°, above 1100 or above 120°. Each possibility represents a separate embodiment of the invention.

Non-limiting examples of suitable hydrophobic materials for the formation of the micro-barrier include different types of epoxy polymers. In certain embodiments, said epoxy polymer is a photoresist material. The photoresist can be selected from a negative photoresist and a positive photoresist. According to further embodiments, the epoxy-based photoresist is SU-8. SU-8 is a commonly used epoxy-based negative photoresist. Negative refers to a photoresist whereby the parts exposed to UV become cross-linked, while the remainder of the film remains soluble and can be washed away during development. SU-8 is composed of Bisphenol A Novolac epoxy that is dissolved in an organic solvent. Bisphenol A (BPA) is an organic synthetic compound with the chemical formula $(CH_3)_2C(C_6H_4OH)_2$ belonging to the group of diphenylmethane derivatives and bisphenols, with two hydroxyphenyl groups. Novolac is a phenol formaldehyde (PF) resin, which is a synthetic polymer obtained by the reaction of phenol or substituted phenol with formaldehyde. SU-8 comprises an average of 8 epoxy groups per moiety.

According to alternative embodiments, the micro-barrier is made of a hydrophilic material. Non-limiting examples of suitable hydrophilic materials include silicon having a silicon dioxide surface, silicon nitride and different types of metal oxides.

According to some embodiments, the micro-barrier is made of an electrically insulating material.

Reference is now made to FIG. 1A, which schematically illustrates a side view of sensor 101 prior to the formation of the sensing layer, according to some embodiments of the invention. Sensor 101 includes substrate 103, having top surface 103a and bottom surface 103b. Sensor 101 further includes micro-barrier 105 having inner face 105a and outer face 105b. Micro-barrier 105 has a circular cross-section and is disposed on substrate top surface 103a. The distance between inner face 105a and outer face 105b is defined as a thickness of micro-barrier 105. Perimeter of inner face 105a is defined as an inner perimeter of micro-barrier 105. Perimeter of outer face 105b is defined as an outer perimeter of micro-barrier 105. Micro-barrier 105 further has top surface 105c. The distance between top surface 105c and top surface 103a of substrate 103 is defined as a height of the micro-barrier.

Sensor 101 further includes an electrode array (hidden from view) disposed on top surface 103a of substrate 103 and surrounded by micro-barrier 105.

Bottom surface 103b of substrate 103 can be disposed on a printed circuit board or printed electronic component. Alternatively, substrate 103 itself can be an integral part of the printed circuit board or printed electronic component.

Figure 1B:
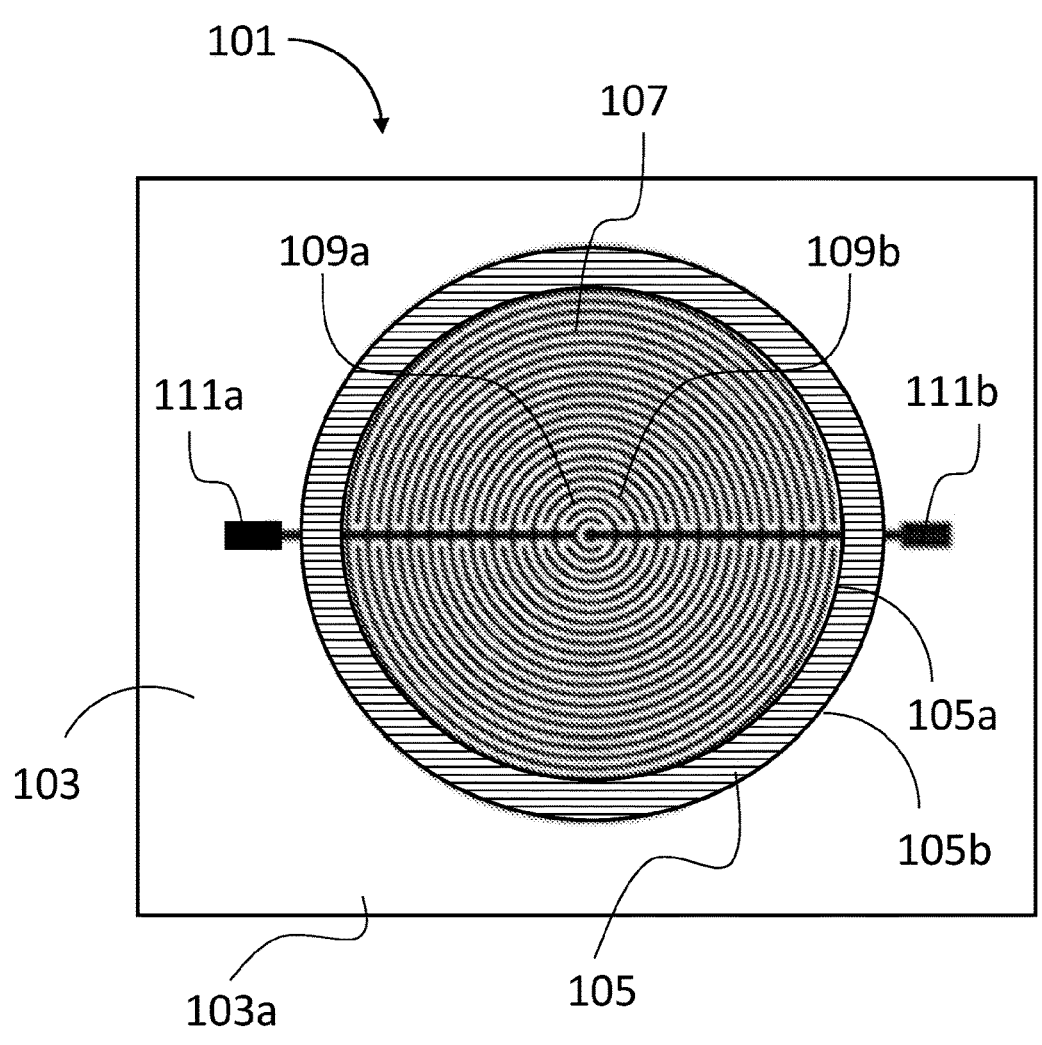
FIG. 1B: Schematic top view representation of a sensor comprising a circular micro-barrier, prior to the formation of the sensing layer.

Reference is now made to FIG. 1B, which schematically illustrates a top view of sensor 101 prior to the formation of the sensing layer, according to some embodiments of the invention. As shown in FIG. 1A, sensor 101 includes substrate 103, having top surface 103a and a bottom surface (hidden from view). Sensor 101 further includes micro-barrier 105 and electrode array 107, disposed on top surface 103a of substrate 103. Micro-barrier 105 has inner face 105a and outer face 105b and surrounds electrode array 107. Perimeter of inner face 105a of micro-barrier 105 is only slightly larger than the outer perimeter of electrode array 107. Electrode array 107 includes a plurality of positive electrodes 109a, connected to contact pin 111a which is disposed outside micro-barrier 105. Electrode array 107 further includes a plurality of negative electrodes 109b, connected to contact pin 111b which is disposed outside micro-barrier 105. The plurality of circular electrodes 109a and 109b are thus contained within micro-barrier 105, wherein contact pins 111a and 111b are located outside the micro-barrier to allow convenient connection to a measuring device (not shown).

Figure 2A:
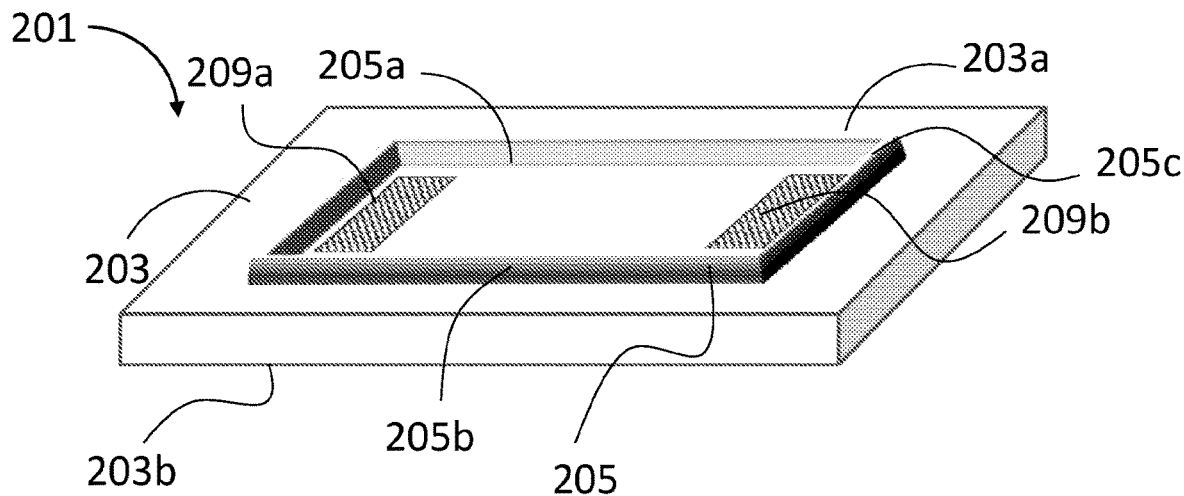
FIG. 2A: Schematic side view representation of a sensor comprising a rectangular micro-barrier, prior to the formation of the sensing layer.

Reference is now made to FIG. 2A, which schematically illustrates a side view of sensor 201 prior to the formation of the sensing layer, according to some embodiments of the invention. Sensor 201 includes substrate 203, having top surface 203a and bottom surface 203b. Sensor 201 further includes micro-barrier 205 having inner face 205a and outer face 205b. Micro-barrier 205 has a rectangular cross-section and is disposed on substrate top surface 203a. The distance between inner face 205a and outer face 205b is defined as a thickness of micro-barrier 205. Perimeter of inner face 205a is defined as an inner perimeter of micro-barrier 205. Perimeter of outer face 205b is defined as an outer perimeter of micro-barrier 205. Micro-barrier 205 further has top surface 205c. The distance between top surface 205c and top surface 203a of substrate 203 is defined as a height of the micro-barrier.

Sensor 201 further includes an electrode array including positive electrode 209a and negative electrode 209b, disposed on top surface 203a of substrate 203 and surrounded by micro-barrier 205. Electrodes 209a and 209b have a rectangular shape.

Figure 2B:
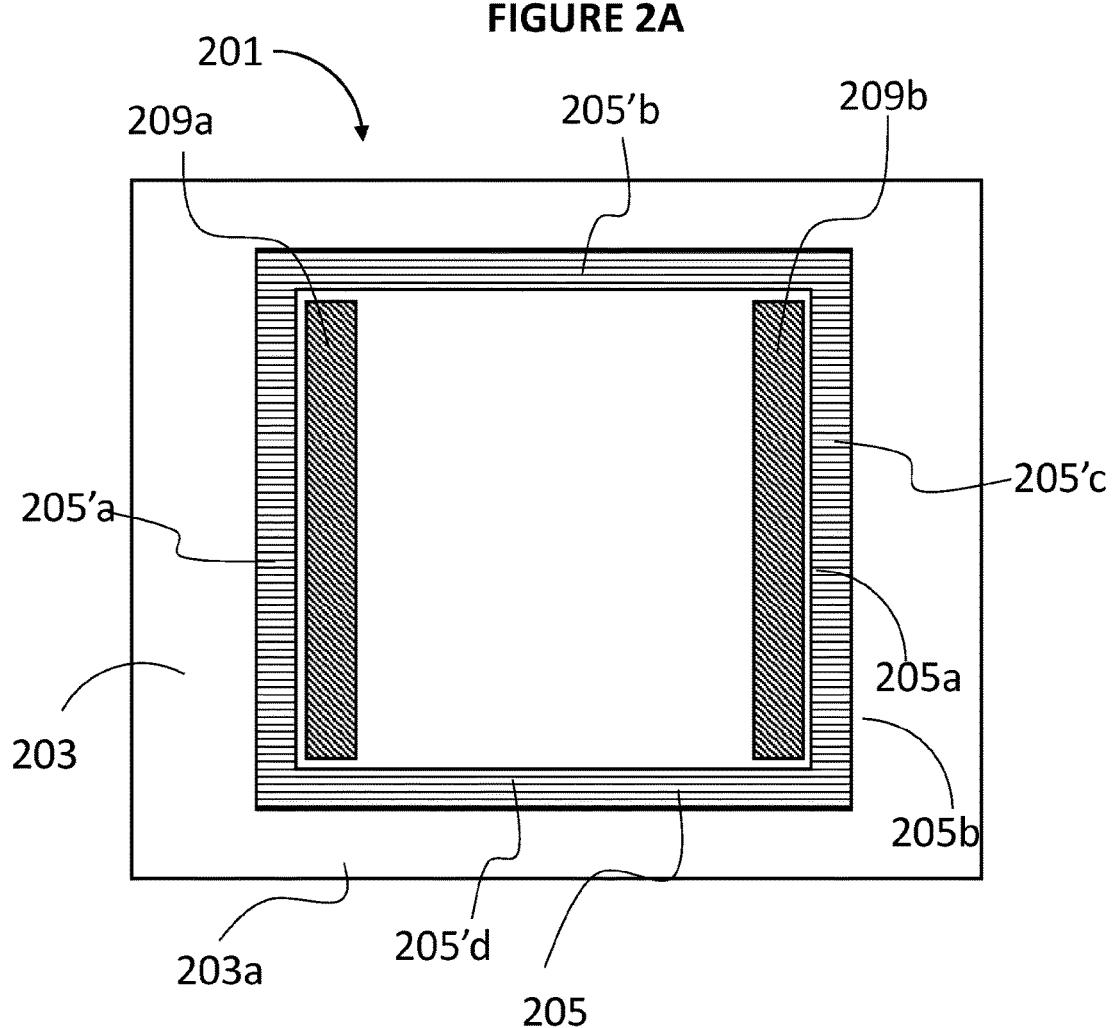
FIG. 2B: Schematic top view representation of a sensor comprising a rectangular micro-barrier, prior to the formation of the sensing layer.

Reference is now made to FIG. 2B, which schematically illustrates a top view of sensor 201 prior to the formation of the sensing layer, according to some embodiments of the invention. As shown in FIG. 2A, sensor 201 includes substrate 203, having top surface 203a and a bottom surface (hidden from view). Sensor 201 further includes micro-barrier 205 and an electrode array including positive electrode 209a and negative electrode 209b, the micro-barrier and the electrodes being disposed on top surface 203a of substrate 203. Micro-barrier 205 has inner face 205a and outer face 205b. Micro-barrier 205 has a rectangular cross-section including sides 205'a, 205'b, 205'c, and 205'd. Electrodes 209a and 209b have a rectangular shape and are disposed within micro-barrier 205, essentially contacting sides 205'a and 205'c of micro-barrier 205, respectively. The length of the electrodes is only slightly smaller than the length of sides 205'a and 205'c of micro-barrier 205.

Sensing Layer

The sensing layer comprises a multiplicity of core-shell particles, which are responsible for the VOCs detection. The term "core-shell particles", as used herein, refers to metal-core organic-shell structures which are obtained, e.g., by coordination chemistry approaches, i.e., by coordinating multifunctional organic ligands to metal nanoparticle cores. In some embodiments, the core-shell particle comprises a metallic core, wherein about 15%-85% of its surface is covered by organic ligands. According to further embodiments, the core-shell particles comprise a monolayer or multilayers of organic ligands.

In some embodiments, the core-shell particles are disposed on the top surface of the substrate in close-packed orientation. The term "close-packed orientation", as used herein, refers in some embodiments to a solid-state arrangement of the MNP cores, wherein organic ligand shells are in contact with their nearest neighbors and in which multiple molecular sized (for example, 0.1 to 3.0 nm) voids among the particles are interconnected. According to further embodiments, the core-sell particles are arranged in a film configuration. The term "film", as used herein, refers in some embodiments to a configuration of well-arranged assembly of metallic nanoparticles, preferably in body centered cubic (BCC) or face centered cubic (FCC) configuration, wherein said MNPs comprise organic ligand shells. It is to be understood that the metallic cores are separated from each other by their own organic ligand shell and the shell of adjacent core-shell particles, and molecular sized voids between said organic ligand shells, and not by a continuous organic film, such as, for example, polymeric film. The film can include one or more layers of the nanoparticles.

Without wishing to being bound by theory or mechanism of action, it is contemplated that upon adsorption of a VOC on an organic ligand of the core-shell particle, a change in structural configuration of the sensing layer occurs. This change can be translated into an electrical signal measured by the electrodes in the electrode array. For example, upon VOCs adsorption the assembly of the core-shell particles can swell or aggregate, leading to a change in the permittivity constant of the sensing layer. The generated electrical signal is determined by the nature of the interaction between the VOC and the sensing layer. The sensors of the present invention are designed to not be limited to any particular VOCs, which can be detected by said sensors.

The metal nanoparticle cores may have any desirable geometry including, but not limited to a cubic, a spherical, and a spheroidal geometry. Each possibility represents a separate embodiment of the present invention. In certain embodiments, the nanoparticle cores have a spherical shape.

The term "nanoparticles" should be understood to include particles having a mean particle size in the range of above 1 nm but below 1000 nm. According to some embodiments, the metal nanoparticle cores have a mean particle size below about 10 nm. According to further embodiments, the metal nanoparticle cores have a mean particle size below about 5 nm. According to some embodiments, the metal nanoparticle cores have a mean particle size in the range of about 1 nm to about 15 nm. According to further embodiments, the metal nanoparticle cores have a mean particle size in the range of about 1 nm to about 10 nm. In yet further embodiments, the metal nanoparticle cores have a mean particle size in the range of about 1.5 nm to about 5 nm. In still further embodiments, the metal nanoparticle cores have a mean particle size in the range of about 1.5 nm to about 3 nm. In yet further embodiments, the metal nanoparticle cores have a mean particle size in the range of about 2 to about 2.5 nm. In some exemplary embodiments, the metal nanoparticle cores have a mean particle size of about 2.2 and about 2.4 nm.

The term "particle size", as used in various embodiments of the invention, refers to the length of the particle in the longest dimension thereof if the particle is not spherical. If the particle is essentially spherical, the term "particle size" refers to the particle diameter. Accordingly, in certain such embodiments, the terms "particle size" and "particle diameter" are used interchangeably.

The term "mean particle size" can refer to the size of monodisperse particles or polydisperse particles. The term "mean particle size", as used herein, refers in some embodiments, to an arithmetic average of particle sizes as can be determined, for example, using Transmission Electron Microscopy (TEM). The mean particle size can further be determined using other techniques known to those of skill in the art including, but not limited to, sedimentation flow fractionation, photon correlation spectroscopy, light scattering, electron scattering, disk centrifugation, and the like.

In certain embodiments, the term "mean particle size below about 15 nm" refers to an arithmetic average of at least about 50% of the particles measured by the above-mentioned techniques. In further embodiments, the term "mean particle size below about 15 nm" refers to an arithmetic average of at least about 70% of the particles, at least about 80% of the particles, at least about 90% of the particles, or at least about 95% of the particles measured by the above-mentioned techniques.

According to some embodiments, the size distribution of the metal nanoparticles cores is narrow. The term "narrow particle size distribution" as used herein, refers to a distribution wherein more than 90% of the particles have a particle size in the range of 0.2-2 times the mean (or average) particle size. Preferably, more than 95% of the particles have a particle size within this range. Even more preferably more than 99% of the particles have a particle size within this range. Nanoparticle size distribution is usually defined in terms of the mean particle size and the width of the distribution. The width of the distribution curve at one half of the maximum value is termed full width at half maximum (FWHM). The relationship between the FWHM and mean particle size is used as a measure of broadness or narrowness of the distribution. In some embodiments, the term "narrow particle size distribution" refers to a distribution wherein the FWHM is less than or equal to 80% of the mean particle size. In some embodiments, the FWHM is less than or equal to 60% of the mean particle size. In other particular embodiments, the FWHM is less than or equal to 40% of the mean particle size.

The metal nanoparticle core can comprise metals and/or metal alloys. Non-limiting examples of suitable metals include Au, Pt, Ag, Ni, Co, Pd, Cu, Al, Zn, Fe, and combinations thereof. The metal alloys can be selected from, but not limited to Au/Pt, Au/Ag, Au/Cu, Au/Ag/Cu, Au/Pd, Au/Ag/Cu/Pd, Pt/Rh, Ni/Co. and Pt/Ni/Fe. Each possibility represents a separate embodiment of the present invention. According to some exemplary embodiments, the metal nanoparticle cores include Au.

In specific embodiments, the organic ligand shell has thickness in the range of about 0.2 nm to about 7 nm. In further embodiments, the organic ligand shell has thickness in the range of about 0.2 nm to about 4 nm. In yet further embodiments, the organic ligand shell has thickness in the range of about 0.2 nm to about 2 nm. In still further embodiments, the organic ligand shell has thickness in the range of about 0.6 nm to about 2 nm. In additional embodiments, the organic ligand shell has thickness in the range of about 2 nm to about 4 nm. In certain embodiments, the organic ligand shell has thickness in the range of about 1.2 nm to about 7 nm. The thickness of the organic ligand shell can be estimated by the nature of the ligands forming said shell, as apparent to a skilled artisan.

The organic ligands forming the shell of the core-shell particles can be selected from small molecules, monomers, oligomers or polymers, preferably short polymeric chains. In some embodiments, the organic ligand is selected from small molecules, monomers, oligomers, and combinations thereof. Each possibility represents a separate embodiment of the invention. In certain embodiments, the sensing layer is devoid of a polymer which is not a part of the organic ligand of the core-shell particle.

Non-limiting examples of the organic ligands suitable for use in the core-shell particles include alkylthiols, e.g., alkylthiols with $C_3$-$C_{24}$ chains, arylthiols, alkylarylthiols, alkylthiolates, ω-functionalized alkylthiolates, arenethiolates, (ω-mercaptopropyl)tri-methyloxysilane, dialkyl sulfides, diaryl sulfides, alkylaryl sulfides, dialkyl disulfides, diaryl disulfides, alkylaryl disulfides, alkyl sulfites, aryl sulfites, alkylaryl sulfites, alkyl sulfates, aryl sulfates, alkylaryl sulfates, xanthates, oligonucleotides, polynucleotides, dithiocarbamate, alkyl amines, aryl amines, diaryl amines, dialkyl amines, alkylaryl amines, arene amines, alkyl phosphines, dialkyl phosphines, aryl phosphines, diaryl phosphines, alkylaryl phosphines, dialkyl phosphines, diaryl phosphines, alkylaryl phosphines, phosphine oxides, alkyl carboxylates, aryl carboxylates, dialkyl carboxylates, diaryl carboxylates, alkylaryl carboxylates, dialkyl carboxylates, diaryl carboxylates, alkylaryl carboxylates, cyanates, isocyanates, peptides, proteins, enzymes, polysaccharides, phospholipids, and combinations and derivatives thereof. Each possibility represents a separate embodiment of the invention.

Additional organic ligands suitable for forming the shells of the core-shell particles include, but are not limited to, alkenyl thiols, alkynyl thiols, cycloalkyl thiols, heterocyclyl thiols, heteroaryl thiols, alkenyl thiolates, alkynyl thiolates, cycloalkyl thiolates, heterocyclyl thiolates, heteroaryl thiolates, alkenyl sulfides, alkynyl sulfides, cycloalkyl sulfides, heterocyclyl sulfides, heteroaryl sulfides, alkenyl disulfides, alkynyl disulfides, cycloalkyl disulfides, heterocyclyl disulfides, heteroaryl disulfides, alkenyl sulfites, alkynyl sulfites, cycloalkyl sulfites, heterocyclyl sulfites, heteroaryl sulfites, alkenyl sulfates, alkynyl sulfates, cycloalkyl sulfates, heterocyclyl sulfates, heteroaryl sulfates, alkenyl amines, alkynyl amines, cycloalkyl amines, heterocyclyl amines, heteroaryl amines, alkenyl carboxylates, alkynyl carboxylates, cycloalkyl carboxylates, heterocyclyl carboxylates, and heteroaryl carboxylates. Each possibility represents a separate embodiment of the invention.

An "alkyl" group refers to a saturated aliphatic hydrocarbon, including straight-chain, branched-chain and cyclic alkyl groups. In one embodiment, the alkyl group has 1-12 carbons designated here as $C_1$-$C_{12}$-alkyl. In another embodiment, the alkyl group has 2-6 carbons designated here as $C_2$-$C_6$-alkyl. In another embodiment, the alkyl group has 2-4 carbons designated here as $C_2$-$C_4$-alkyl. In an exemplary embodiment, the alkyl group has 3-24 carbons designated here as $C_3$-$C_{24}$ alkyl. The alkyl group may be unsubstituted or substituted by one or more groups selected from halogen, haloalkyl, acyl, amido, ester, cyano, nitro, and azido. Each possibility represents a separate embodiment of the invention.

A "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

An "alkenyl" group refers to an aliphatic hydrocarbon group containing at least one carbon-carbon double bond including straight-chain, branched-chain and cyclic alkenyl groups. In one embodiment, the alkenyl group has 2-8 carbon atoms (a $C_{2-8}$ alkenyl). In another embodiment, the alkenyl group has 2-4 carbon atoms in the chain (a $C_{2-4}$ alkenyl). Exemplary alkenyl groups include, but are not limited to, ethenyl, propenyl, n-butenyl, i-butenyl, 3-methylbut-2-enyl, n-pentenyl, heptenyl, octenyl, cyclohexylbutenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 2-8 carbon atoms in the chain (a $C_{2-8}$ alkynyl). In another embodiment, the alkynyl group has 2-4 carbon atoms in the chain (a $C_{2-4}$ alkynyl). Exemplary alkynyl groups include, but are not limited to, ethynyl, propynyl, n-butynyl, 2-butynyl, 3-methylbutynyl, n-pentynyl, heptynyl, octynyl and decynyl. An alkylalkynyl is an alkyl group as defined herein bonded to an alkynyl group as defined herein. The alkynyl group can be unsubstituted or substituted through available carbon atoms with one or more groups defined hereinabove for alkyl.

An "aryl" group refers to an aromatic monocyclic or multicyclic ring system. In one embodiment, the aryl group has 6-10 carbon atoms. The aryl is optionally substituted with at least one "ring system substituents" and combinations thereof as defined herein. Exemplary aryl groups include, but are not limited to, phenyl or naphthyl. An alkylaryl is an alkyl group as defined herein bonded to an aryl group as defined herein. The aryl group can be unsubstituted or substituted through available carbon atoms with one or more groups defined hereinabove for alkyl.

A "heteroaryl" group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

A "heterocyclic ring" or "heterocyclyl" group refers to five-membered to eight-membered rings that have 1 to 4 heteroatoms, such as oxygen, sulfur and/or in particular nitrogen. These five-membered to eight-membered rings can be saturated, fully unsaturated or partially unsaturated, with fully saturated rings being preferred. Exemplary heterocyclic rings include, but are not limited to, piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. An alkylheterocyclyl is an alkyl group as defined herein bonded to a heterocyclyl group as defined herein. The heterocyclyl group can be unsubstituted or substituted through available atoms with one or more groups defined hereinabove for alkyl.

"Ring system substituents" refer to substituents attached to aromatic or non-aromatic ring systems including, but not limited to, H, halo, haloalkyl, ($C_1$-$C_8$)alkyl, ($C_2$-$C_8$)alkenyl, ($C_2$-$C_8$)alkynyl, ($C_6$-$C_{10}$)aryl, acyl, amido, ester, cyano, nitro, azido, and the like.

A "halogen" or "halo" group as used herein alone or as part of another group refers to chlorine, bromine, fluorine, and iodine. The term "haloalkyl" refers to an alkyl group having some or all of the hydrogens independently replaced by a halogen group including, but not limited to, trichloromethyl, tribromomethyl, trifluoromethyl, triiodomethyl, difluoromethyl, chlorodifluoromethyl, pentafluoroethyl, 1,1-difluoroethyl bromomethyl, chloromethyl, fluoromethyl, iodomethyl, and the like.

An "acyl" group as used herein encompasses groups such as, but not limited to, formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Currently preferred acyl groups are acetyl and benzoyl. An "alkoxy" group refers to an —O-alkyl group wherein R is alkyl as defined above.

A "thio" group as used herein alone or as part of another group refers to an SH group. The terms "alkylthio", "arylthio" or "arylalkylthio" as used herein alone or as part of another group refer to any of the above alkyl, arylalkyl or aryl groups linked to a sulfur atom.

According to certain embodiments, the organic ligand is selected from the group consisting of alkylthiols, arylthiols, alkylarylthiols, alkylthiolates, ω-functionalized alkanethiolates, arenethiolates, (γ-mercaptopropyl)tri-methyloxysilane, dialkyl disulfides and combinations and derivatives thereof. Each possibility represents a separate embodiment of the present invention. According to a specific embodiment, alkylthiol or alkylarylthiol is selected from the group consisting of dodecanethiol, 2-ethylhexanethiol, 3-ethoxythiophenol, 2-ethoxythiophenol, decanethiol, 2-nitro-4-(trifluoromethyl)benzenethiol, butanethiol, benzyl mercaptan, octadecanethiol, 2-naphthalenethiol, 4-chlorobenzenemethanethiol, tert-dodecanethiol, hexanethiol, octadecanethiol, 1-methyl-2-imidazolethiol and combinations thereof. According some exemplary embodiments, the organic ligand comprises an alkylthiol selected from dodecanethiol and 2-ethylhexanethiol.

The core-shell particles can include either hydrophobic ligands or hydrophilic ligands. Each possibility represents a separate embodiment of the present invention.

According to some exemplary embodiments, the core-shell particles comprise hydrophobic ligands. The hydrophobic ligand can be selected from the group consisting of dodecanethiol, 2-ethylhexanethiol, decanethiol, hexanethiol, dibutyl disulfide, 4-tert methylbenzenethiol, 1-heptanethiol, butanethiol, benzylmercaptan, 3-ethoxytiophenol, tert-dodecanethiol and combinations thereof. Each possibility represents a separate embodiment of the present invention.

According to some embodiments, the core-shell particles comprise hydrophilic ligands. The hydrophilic ligand can be selected from the group consisting of 2-nitro-4-trifluoromethylbenzenthiol, 4-chlorobenzenmethanethiol and combinations thereof. Each possibility represents a separate embodiment of the present invention.

In accordance with the choice of the organic ligand, the sensing layer can be either hydrophobic or hydrophilic. Each possibility represents a separate embodiment of the invention. Hydrophobicity of the sensing layer can be determined by the type of organic ligands used to functionalize the metallic nanoparticle cores. The hydrophobicity of the sensing layer can further be determined by depositing the sensing layer material (i.e., core-shell particles from the corresponding dispersion) onto the substrate and measuring water contact angle after solvent evaporation.

In some currently preferred embodiments, the sensing layer is hydrophobic and the micro-barrier is made of a hydrophobic material.

In additional embodiments, the sensing layer is hydrophilic. In further embodiments, the micro-barrier is made of a hydrophilic material.

The sensing layer can have any shape or geometry as known in the art, such as, but not limited to, circular, oval, square, rectangular, triangular, hexagonal, and polygonal shape. The area of the sensing layer can range from about 0.03 mm$^2$ to about 20 mm$^2$. In further embodiments, the area of the sensing layer ranges from about 0.1 mm$^2$ to about 10 mm$^2$, or from about 0.5 mm$^2$ to about 5 mm$^2$. Each possibility represents a separate embodiment of the invention. In certain embodiments, the surface area of the sensing layer is about 1 mm$^2$. It is to be understood that the shape and the surface area of the sensing layer are dictated by the shape and the area of the micro-barrier cross-section. In some embodiments, the area of the sensing layer is essentially the same as the cross-sectional area of the micro-barrier.

The sensing layer is disposed on the substrate and is in electric contact with the electrode array. In some embodiments, the sensing layer is disposed on top of the electrode array. The term "in electric contact with the electrode array", as used herein refers to an electric contact with at least one positive electrode and at least one negative electrode of the electrode array.

As mentioned hereinabove, one of the beneficial features of the sensors of the present invention is that the morphology of the sensing layer can be effectively controlled.

Accordingly, in some embodiments, the sensing layer has a substantially uniform thickness throughout the entire area thereof. The term "substantially uniform", as used herein, refers in some embodiments to the variance of less than about 10% in the sensing layer thickness between the outer perimeter of the sensing layer and the remaining surface. The thickness of the sensing layer can be determined, inter alia, by Atomic Force Microscopy (AFM).

Chemically Sensitive Sensor

Figure 3:
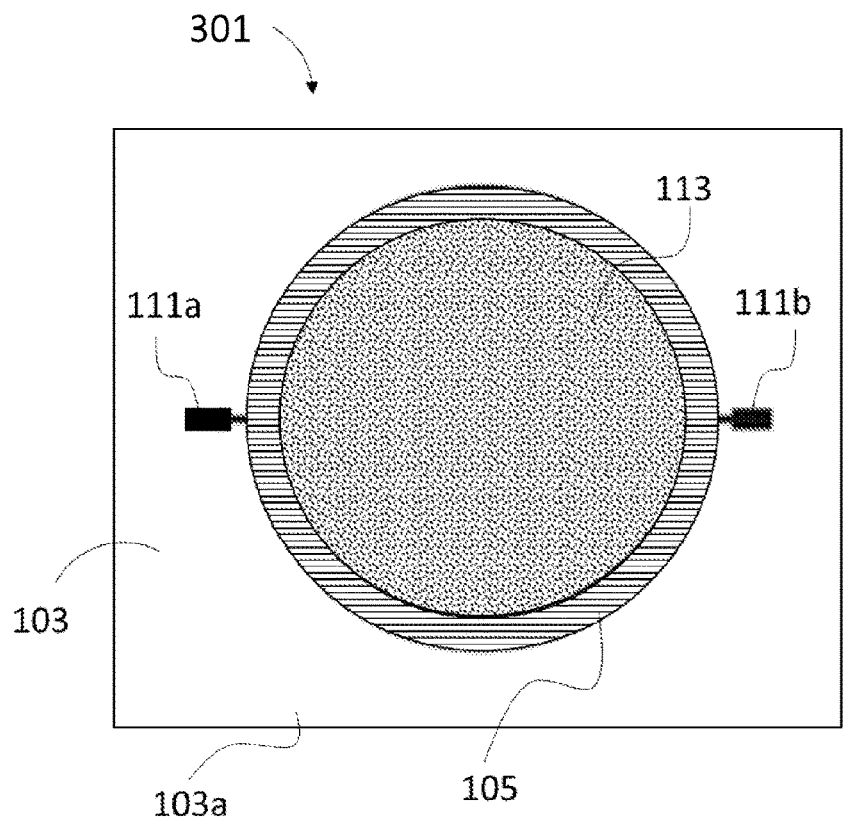
FIG. 3: Schematic top view representation of a sensor comprising a circular micro-barrier and a sensing layer.

Reference is now made to FIG. 3, which schematically illustrates a top view of sensor 301 comprising a sensing layer, according to some embodiments of the invention. Similarly, to sensor 101 shown in FIG. 1B, sensor 301 includes substrate 103, having top surface 103a. Sensor 301 further includes micro-barrier 105 and electrode array comprising a plurality of circular electrodes (hidden from view) and contact pins 111a and 111b, disposed on top surface 103a of substrate 103. Sensor 301 further includes sensing layer 113, which is disposed on top of the electrode array and is surrounded by micro-barrier 105. The area of sensing layer 113 is essentially the same as the cross-sectional area of micro-barrier 105.

Figure 4:
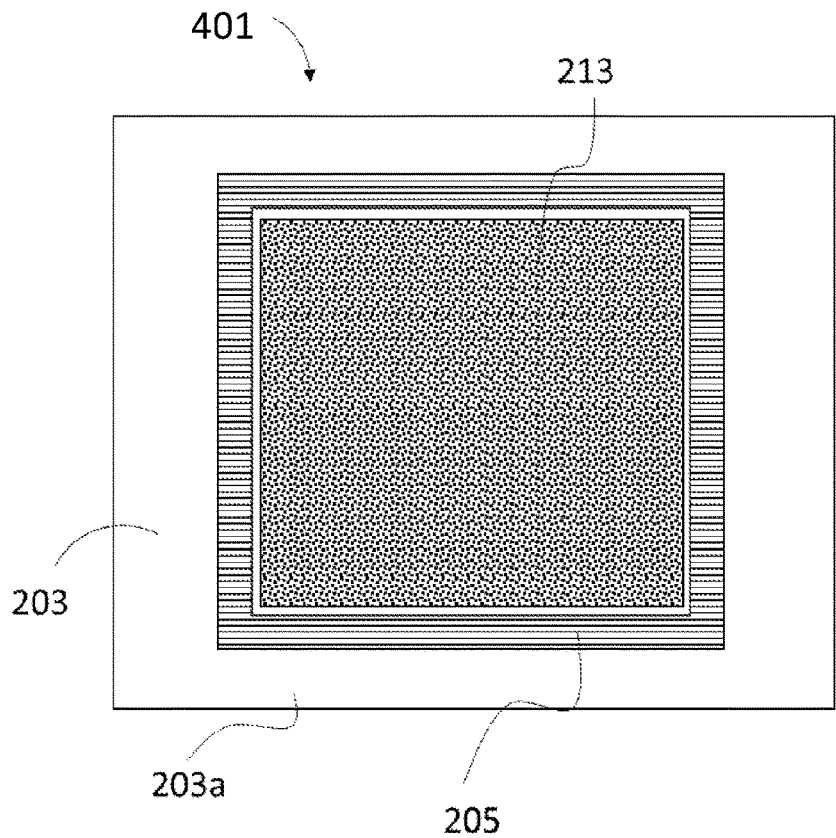
FIG. 4: Schematic top view representation of a sensor comprising a rectangular micro-barrier and a sensing layer.

Reference is now made to FIG. 4, which schematically illustrates a top view of sensor 401 including a sensing layer, according to some embodiments of the invention. Similarly, to sensor 201 shown in FIG. 2B, sensor 401 includes substrate 203, having top surface 203a. Sensor 401 further includes micro-barrier 205 and an electrode array including a positive electrode and a negative electrode (hidden from view), the micro-barrier and the electrodes being disposed on top surface 203a of substrate 203. Sensor 401 further includes sensing layer 213 disposed on top surface 203a of substrate 203, covering the electrodes. The area of sensing layer 213 is essentially the same as the cross-sectional area of micro-barrier 205.

The sensor of the present invention can be configured, e.g., as a capacitive sensor, resistive sensor, chemiresistive sensor, impedance sensor, field effect transistor sensor, strain gauge sensor and the like. Each possibility represents a separate embodiment of the present invention. In a non-limiting example, the sensor of the present invention is configured as a chemiresistive sensor (i.e., chemiresistor). A change in resistance of such sensor is produced by the swelling or aggregation of the assembly of the core-shell particles in response to the adsorption of the VOCs, which proceeds through various chemical interactions. The interactions include, but are not limited to, hydrogen-bonding, host-guest, van der Waals, electrostatic, charge-transfer, antigen-antibody interactions, and combinations thereof. As used herein, the term "swelling" refers to an increase of the average inter-particle distance in the assembly of core-shell particles. As used herein, the term "aggregation" refers to a decrease of the average inter-particle distance in the assembly of core-shell particles. Changes in permittivity (translated into the measured change in resistance) usually occur in thin films having regions of voids in the sensing layer being composed of 2D or 3D films of organically capped metallic nanoparticles.

In some embodiments, the sensor of the invention is configured to detect VOCs in a test sample. The test sample, according to the principles of the present invention is selected from a gas sample, such as, for example, air or breath, and a fluid sample, e.g., bodily fluid or secretion. In some embodiments, the sensor is configured to provide the detection of the presence and concentration of the analyte molecules in the surrounding environment. Non-limiting examples of analytes, which can be detected by the sensor, include VOCs selected from octane, benzaldehyde, hexane, hexanal, ethyl hexanol, octanol and trimethylbenzene. In some exemplary embodiments, said VOC is octane In some embodiments, the sensor comprises a plurality of electrode arrays, respective micro-barriers and respective sensing layers disposed on a single substrate. In certain such embodiments, the sensor is also termed sensor array. Arrangement of the sensors can be performed as is known in the art. Non-limiting arrangement includes a matrix of sensors (rows and/or columns) comprising a plurality of sensors, for example between 2 and 20 sensors, wherein each sensor independently generates an electrical signal in response to VOCs sensing. The core-shell nanoparticles of the plurality of sensing layers can be the same or different. In some embodiments, the sensor array comprises sensors having MNP cores of a single species capped with various organic ligand shells. In alternative embodiments, the sensor array comprises sensors having MNP cores of various species.

Sensor Signal Measurement and Analyzing Devices

The signal of the chemically sensitive sensor can be detected and/or measured by a suitable detection device. Thus, in some embodiments, the platform unit or its sensor is coupled to the signal detection and/or measuring device. Suitable detection and/or measuring devices should be susceptible to a change in any one or more of resistance, conductance, alternating current (AC), frequency, capacitance, impedance, inductance, mobility, electrical potential, piezoelectricity, and voltage threshold. Each possibility represents a separate embodiment of the present invention. In certain embodiments, the detection and/or measuring device is susceptible to a change in resistance or conductance of the sensor. In additional embodiments, the measuring devices are susceptible to swelling or aggregation of the core-shell particles. Changes in the electric properties of the sensor, such as resistance, conductance, direct or alternating current, capacitance, impedance, electrical potential, or voltage threshold can be measured by any suitable device known in the art, including, inter alia, a data logger, a potentiostat, a voltmeter, a conductivity meter, an LCR meter or a millimeter. Changes in the piezoelectricity properties of the sensor set can be measured using, for example, a piezoelectric sensor. The measured signals can be displayed on a display or transmitted to a host computer.

When a plurality of sensors is used, the signals obtained from the sensors can be analyzed by a computing system configured for executing various algorithms stored on a non-transitory memory. Thus, according to some embodiments, the chemically sensitive sensor or sensor array is coupled to said computing system. The algorithms can include learning and pattern recognition algorithms, such as, but not limited to, artificial neural network (ANN) algorithm, support vector machine (SVM), discriminant function analysis (DFA), principal component analysis (PCA), multilayer perception (MLP), generalized regression neural network (GRNN), fuzzy inference system (FIS), self-organizing map (SOM), radial bias function (RBF), genetic algorithm (GAS), neuro-fuzzy system (NFS), adaptive resonance theory (ART), partial least squares (PLS), multiple linear regression (MLR), principal component regression (PCR), linear discriminant analysis (LDA), cluster analysis, nearest neighbor, Fisher linear discriminant analysis (FLDA), soft independent modeling of class analogy (SIMCA), K-nearest neighbors (KNN), genetic algorithms, and fuzzy logic algorithms and canonical discriminant analysis (CDA).

Method of Fabrication of the Chemically Sensitive Sensor

The step of forming an electrode array can include depositing a metal onto the top surface of the substrate. Non-limiting methods of metal deposition include e-beam evaporation, physical vapor deposition, sputter-deposition, drop-casting, field enhanced deposition, soft lithography, inkjet printing, and screen printing. The metal can be selected from Au, Pt, Ti, Cu, Ag, Pd, Pt, Ni, Al, and combinations thereof.

In certain embodiments, the step of forming an electrode array comprises applying a shadow mask to the top surface of the substrate during metal deposition. The shadow mask can be fabricated by any suitable process as known in the art. For example, a silicon wafer can be used, wherein a photoresist pattern is applied to the wafer and the wafer is etched for removing the silicon which is not protected by the photoresist.

The micro-barrier can be formed by a method selected from photolithography, e-beam lithography, direct evaporation/sputtering through shadow mask, soft (stamp) contact, inkjet printing. According to certain embodiments, formation of the micro-barrier is carried out by a photolithography process.

According to some embodiments, the photolithography process includes a step of applying a negative photoresist to the substrate, and, optionally, to the electrode array. The negative photoresist can include an epoxy-based photoresist. In certain embodiments, said negative photoresist is SU-8. SU-8 is particularly suitable for use in the fabrication method of the present invention, as it enables formation of relatively thick (hundreds of micrometers) structures with nearly vertical side walls.

The photoresist material can be applied to the surface of the substrate by any suitable method, such as, for example, spin-coating, or casting. In some currently preferred embodiments, the photoresist is applied by spinning. In certain embodiments, the photoresist is applied by spinning at a rate ranging from about 200 rpm to about 5000 rpm. In further embodiments, spinning is performed at a rate ranging from about 500 rpm to about 2000 rpm. In some embodiments, the photoresist is applied by increasing the spinning rate from about 500 rpm to about 2000 rpm. The spinning time can range from about 5 to about 120 seconds.

According to some embodiments, the photolithography process further includes a step of disposing a mask with a predefined pattern on the negative photoresist. The mask can have a ring-shaped opening in a shape selected from circular, oval, square, rectangular, triangular, hexagonal, and polygonal ring shape. Each possibility represents a separate embodiment of the invention. The mask can be fabricated as described hereinabove in connection with the electrode array fabrication.

According to some embodiments, the photolithography process further includes a step of exposing the negative photoresist to UV irradiation, wherein the photoresist is covered by the mask. The UV light intensity and exposure time can be selected based on the type and thickness of the applied photoresist. In some exemplary embodiments, the photoresist is exposed to UV light with an intensity of 14 mW/cm$^2$ for 6 seconds.

According to some embodiments, the photolithography process further includes a step of developing the remaining negative photoresist. The developer can be selected based on the photoresist type. In some exemplary embodiments, the photoresist was SU-8 and the developer was propylene glycol methyl ether acetate (PGMEA), wherein the development process lasted for about 1 minute.

According to some embodiments, the substrate is heated to remove moisture and any possible remaining solvents prior to the application of the photoresist. According to some embodiments, the substrate with the photoresist is heated following the application of the photoresist, following the UV exposure step, and/or following the development step. The heating can be performed at a temperature ranging from about 80° C. to about 200° C. for 1 to 30 minutes.

According to some embodiments, the photolithography process does not include plasma cleaning following the development state. It was found by the inventors that oxygen plasma treatment of the micro-barrier photoresist material decreased its hydrophobicity, thereby potentially weakening the coffee ring elimination effect.

According to some currently-preferred embodiments, the photolithography process does not include a step of photoresist lift-off, thereby preventing abrasion of the micro-barrier structure and in particular the inner face thereof As mentioned hereinabove, the step of forming a sensing layer comprises applying a dispersion comprising the core-sell particles and a solvent onto the electrode array within the micro-barrier. The core-shell particles can contain the metallic nanoparticle core and the organic ligand shell as described hereinabove. The synthesis of the core-shell particles can be carried out by various methods known in the art, for instance, by the two-phase method (Brust et al., *J. Chem. Soc. Chem. Commun.*, 801, 1994, 2) with some modifications (Hostetler et al., *Langmuir*, 14 1998, 24), using a variety of organic ligands to provide widely selective adsorption sites for VOCs adsorption. In some exemplary embodiments, gold-based core-shell particles were synthesized by transferring $AuCl_4^-$ from aqueous $HAuCl_4 \cdot xH_2O$ solution to a toluene solution by the phase-transfer reagent TOAB. After isolating the organic phase, excess thiols with toluene solution are added to the solution. The mole ratio of thiol:$HAuCl_4 \cdot xH_2O$ can vary between 1:1 and 10:1, depending on the thiol used. After vigorous stirring of the solution, aqueous solution of reducing agent $NaBH_4$ in large excess is added. The reaction is constantly stirred at room temperature for at least 3 hours to produce a dark brown solution of the thiol-capped Au nanoparticles. The resulting solution can be further subjected to solvent removal in a rotary evaporator followed by multiple washings using ethanol and toluene.

Suitable solvents for suspending the obtained core-shell particles can be selected from hydrophobic (or non-polar) and hydrophilic (or polar) solvents, based on the type of the organic ligand used. Non-limiting examples of suitable solvents include toluene, 2-pentatone, hexane, ethanol, acetone, isopropyl, 2-pentanone, water and combinations thereof. In certain embodiments, the solvent is selected from toluene, 2-pentatone, and hexane.

As used herein, the term "dispersion" refers broadly to a heterogeneous mixture containing solid substances dispersed throughout liquid substances with or without the presence of dispersing agents, wherein the solid substances are either uniformly dispersed or sedimented. The term "dispersion" includes suspensions and colloids.

As used herein, the term "suspension" refers to a heterogeneous mixture containing solid particles that are sufficiently large for sedimentation. The internal phase (solid) is dispersed throughout the external phase (liquid) through agitation with or without the presence of dispersing agents. In certain embodiments, the dispersion comprises the core-shell particles in a form of a suspension.

In some currently preferred embodiments, the dispersion of the core-shell particles is hydrophobic and the micro-barrier material is hydrophobic. In additional embodiments, the dispersion of the core-shell particles is hydrophilic and the micro-barrier material is hydrophilic.

According to certain embodiments, the sensing layer is manufactured through a self-assembly process to produce a film comprising the core-shell particles. The term "self-assembly" as used herein refers to a process of organization of molecules without intervening from an outside source. The self-assembly process takes place in a solution/solvent or directly on the solid-state substrate.

Exemplary method for obtaining well-ordered two-dimensional assemblies of core-shell particles includes, but is not limited to, random deposition from dispersion or dispersion of cores-shell particles on solid surfaces. The deposition can be performed by inkjet printing or drop casting.

According to certain embodiments, the dispersion is applied by inkjet-printing. Inkjet printing is typically used for printing on solid-state or flexible substrates using an inkjet printer designated for printed electronics. A dispersion containing the core-shell particles is used as a filling material (or "ink") of the printing head according to procedures well known in the art, as described in e.g., Holland et al. (*Ink Maker* 8, 83, 2005).

According to some embodiments, the core-shell particles dispersion is applied onto the substrate, such that the formed sensing layer is in electric contact with the electrode array. In some embodiments, the dispersion is applied on top of the electrode array.

In some embodiments, the dispersion s applied to the center of the electrode array.

The volume of the dispersion, which is deposited onto the substrate, and optionally, the electrode array, can be adjusted to form a drop, having essentially the same height as the height of the micro-barrier. The desired volume can be deposited as a multiplicity of precisely measured drops of a smaller volume, such as, for example, 0.3 nL or 1 nL. In certain embodiments, the dispersion is applied in a total volume ranging from about 5 nL to about 500 nL. In further embodiments, the dispersion is applied in a total volume ranging from about 5 nL to about 150 nL. In some exemplary embodiments, the dispersion is applied in a total volume ranging from about 20 nL to about 300 nL. In a particular embodiment, the applied total volume ranges from about 20 nL to about 120 nL.

The concentration of the core-shell particles in the dispersion can range from about 1 mg/ml to about 100 mg/ml. In some exemplary embodiments, the concentration of the core-shell particles in the dispersion ranges from about 5 mg/ml to about 20 mg/ml According to some embodiments, the step of forming the sensing layer further includes a drying step to allow solvent evaporation.

Chemically Sensitive Sensor Applications

Due to the miniaturized dimensions of the sensor (in the range of a few micrometers), it could be installed in any electronic device including, but not limited to, a watch or cellular phone. The integration of the sensor array to a commonly used electronic device allows it to be used for monitoring health of a subject, as well as diagnosing various diseases.

The sensor of the present invention can be used in various additional applications wherein the detection of VOCs is feasible. These applications include, but are not limited to, environmental toxicology and remediation, medicine, materials quality control, food and agricultural products monitoring, heavy industrial manufacturing (automotive, aircraft, etc.), such as ambient air monitoring, worker protection, emissions control, and product quality testing; oil/gas petrochemical applications, such as combustible gas detection, $H_2S$ monitoring, hazardous leak detection and identification; hazardous spill identification, enclosed space surveying, utility and power applications, such as emissions monitoring and transformer fault detection; food/beverage/agriculture applications, such as freshness detection, fruit ripening control, fermentation process monitoring and control, flavor composition and identification, product quality and identification, and refrigerant and fumigant detection.

Additional applications include, but are not limited to, cosmetic/perfume applications, such as fragrance formulation, product quality testing, and fingerprinting; chemical/plastics/pharmaceuticals applications, such as fugitive emission identification, leak detection, solvent recovery effectiveness, perimeter monitoring, and product quality testing; hazardous waste site applications, such as fugitive emission detection and identification, leak detection and identification, transportation applications, such as hazardous spill monitoring, refueling operations, shipping container inspection, and diesel/gasoline/aviation fuel identification; building/residential applications, such as natural gas detection, formaldehyde detection, smoke detection, automatic ventilation control (cooking, smoking, etc.), and air intake monitoring; hospital/medical applications, such as anesthesia and sterilization gas detection, infectious disease detection, breath, wound and bodily fluids analysis, and telesurgery.

As used herein and in the appended claims the singular forms "a", "an," and "the" include plural references unless the content clearly dictates otherwise. Thus, for example, reference to "an organic ligand" includes a plurality of such organic ligands and equivalents thereof known to those skilled in the art, and so forth. It should be noted that the term "and" or the term "or" is generally employed in its sense including "and/or" unless the content clearly dictates otherwise.

As used herein, the term "about", when referring to a measurable value such as an amount, a temporal duration, and the like, is meant to encompass variations of +/−10°/%, more preferably +/−5%, even more preferably +/−1%, and still more preferably +/−0.1% from the specified value, as such variations are appropriate to perform the disclosed methods.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Fabrication of the Chemically Sensitive Sensor

The sensor was designed to include eight electrode arrays, wherein eight micro-barriers were disposed on the top surface of a solid substrate and surrounded each electrode array.

Electrode Array Fabrication

First, circular inter-digitated platinum electrodes were fabricated by electron-beam evaporator (Evatec BAK501) on silicon wafer comprising a thermal silicon oxide film of 1 µm (purchased from Nova Electronic Materials, LLC, USA). The outer diameter of each electrode array was 1000 µm. The electrode thickness was 10 µm, each two adjacent electrodes being separated by a spacing of 10 µm.

Micro-Barrier Preparation

Figure 5:
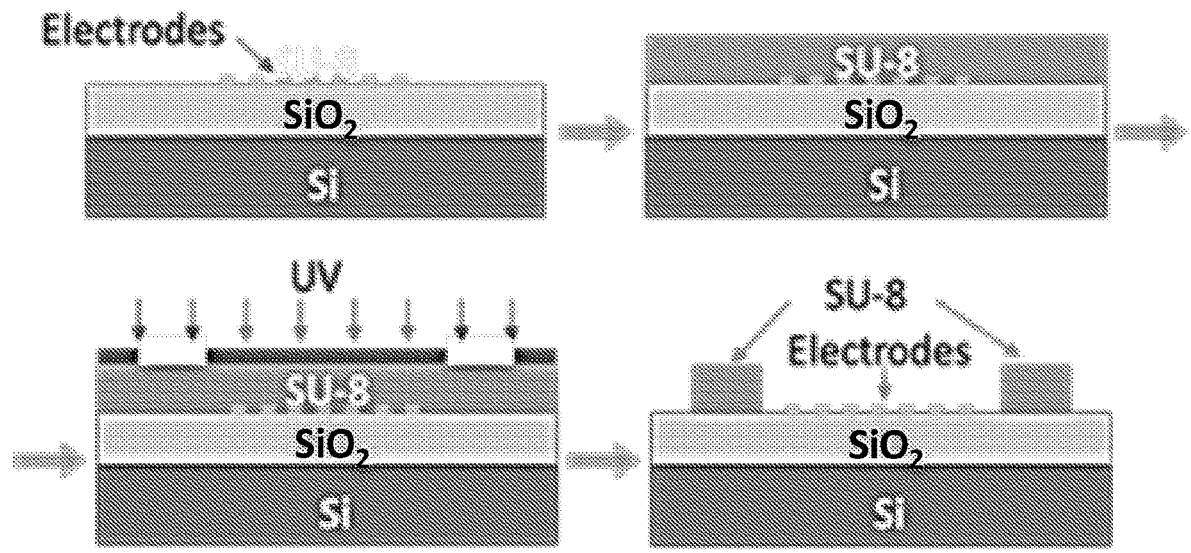
FIG. 5: Schematic illustration of epoxy-based micro-barrier preparation process.

A schematic representation of SU-8 micro-barrier preparation is shown in FIG. 5. The SU-8 micro-barrier was made using a photolithography process in clean room facilities. The wafer comprising eight electrode arrays was heated by a hot plate at 120° C. for 5 minutes. After the wafer was cooled down to room temperature, it was coated with negative photoresist SU-8 2002 (purchased from MicroChem Corp., MA, USA) by using a spinner with gradual acceleration (500 rpm for 10 sec, and then an additional spinning of 2000 rpm for 30 sec). Then the wafer was heated by a hot plate at 95° C. for 2 minutes followed by UV light exposing through a special mask with intensity of 14 mW/cm$^2$ for 6 sec. Then the negative photoresist was developed for 1 min using PGMEA developer and washed with isopropyl alcohol. Curing of said wafer was performed by heating on a hot plate at 150° C. for 15 minutes. The height of the micro barrier was 2.35±0.05 µm.

Three types of wafers were fabricated, which differ in their height, including 2.4, 5.5 and 17.0 µm. The thickness of the micro-barriers was 100 µm and their inner diameter was about 1000 µm in each case.

Core-Shell Particles Synthesis

Core-shell particles including thiol-capped Au NPs were synthesized using two-phase method according to Brust et al. (J. Chem. Soc., Chem. Com., 1994, 2, 801-802). $AuCl_4$ was first transferred from aqueous $HAuCl_4 \cdot xH_2O$ solution to a toluene solution by the phase-transfer reagent. After the organic phase was isolated, solution of thiol and toluene was added to the gold dispersion. The mole ratios of thiol:Au were 0.8:1 for dodecanethiol and 0.7:1 for 2-ethylhexanethiol-capped Au NPs. After vigorous stirring of the solution for 10 min, aqueous solution of reducing agent $NaBH_4$ in large excess (25 mL, 0.4 M, ice-cooled) was added. The reaction was stirred at room temperature for at least 3 hours, which produced a dark brown dispersion of the thiol-capped Au NPs. The resulting dispersion was subjected to solvent removal in a rotary evaporator and followed by multiple washings using ethanol and toluene.

Inkjet-Printing of Thiol-Capped Au NPs Dispersion

The core-shell particles dispersion was deposited onto the substrate and the electrode arrays by nanoprinter dispenser system sciFLEXARRAYER S3 (Scienion company, Germany), a non-contact piezo-dispensing system that allows dispersion of precise drops of 0.3±0.05 nanoliter. This inkjet-printing technique allowed dropping the thiol-capped gold NPs dispersion exactly at the middle of the electrode array.

Figure 6:
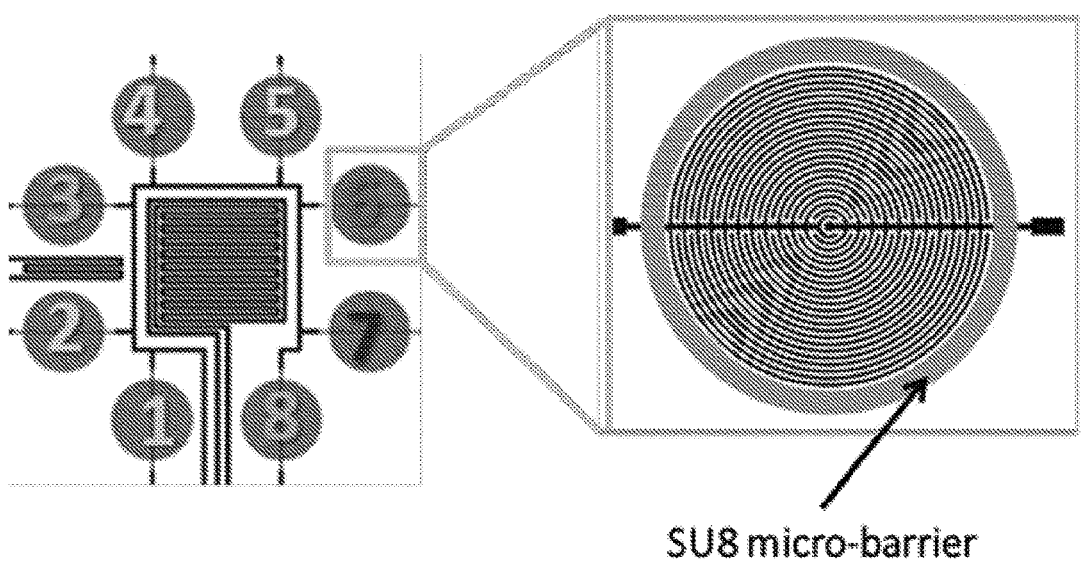
FIG. 6: Schematic illustration of a sensor device comprising eight sensing layers disposed within corresponding micro-barriers and a resistor for temperature control.

The obtained device is shown in FIG. 6. The device consists of eight sensors and a resistor (in the middle) for temperature control. Each sensor is a chemically sensitive sensor comprising gold nanoparticle cores with specific organic ligands shells.

Example 2: Characterization of the Dispersions of the Core-Shell Particles

Figure 7A:
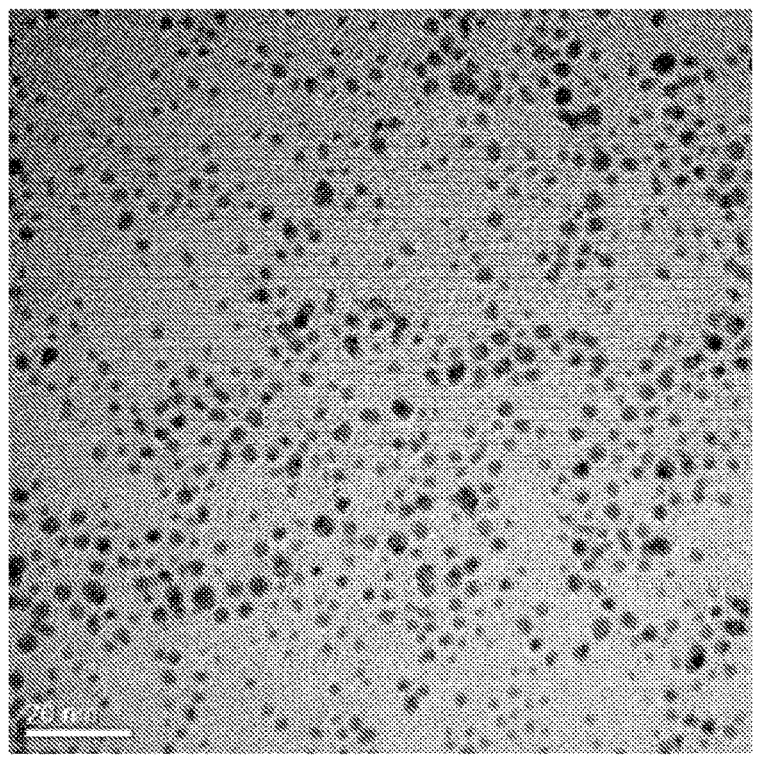
FIG. 7A: Transmission-electron microscopy (TEM) image of dodecanethiol-capped Au nanoparticles (NPs) dispersion.
Figure 7B:
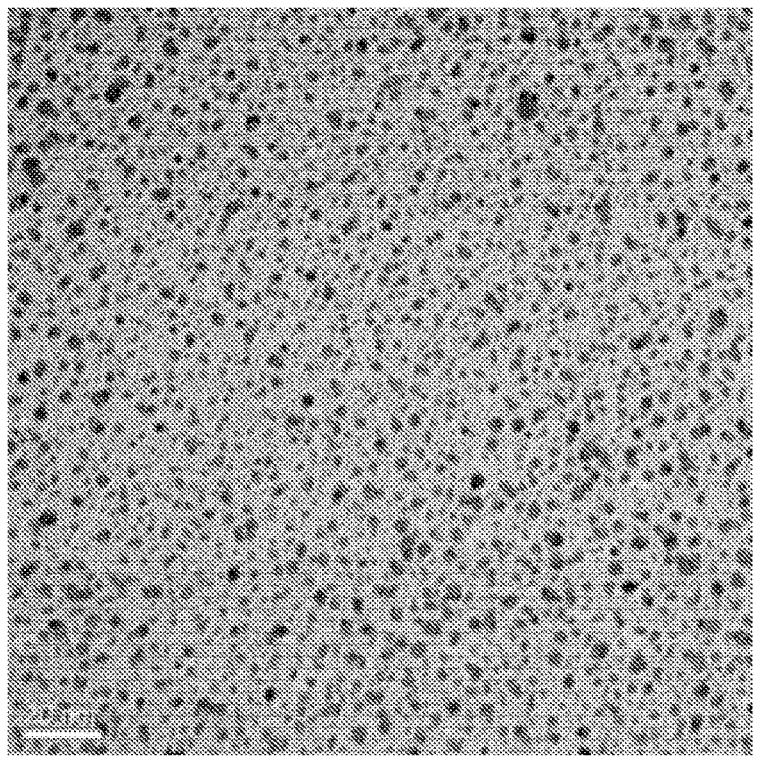
FIG. 7B: TEM image of 2-ethylhexaethiol-capped Au NPs dispersion.
Figure 7C:
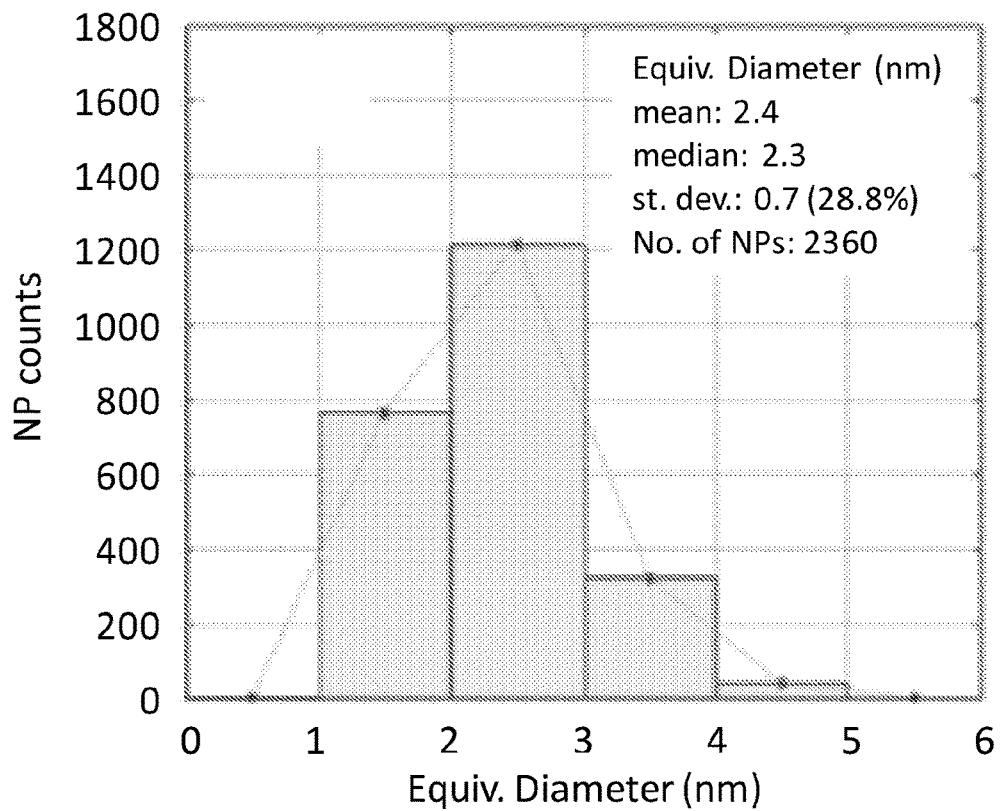
FIG. 7C: Core size distribution of dodecanethiol-capped Au NPs having a narrow size distribution with an average diameter of about 2.4 nm
Figure 7D:
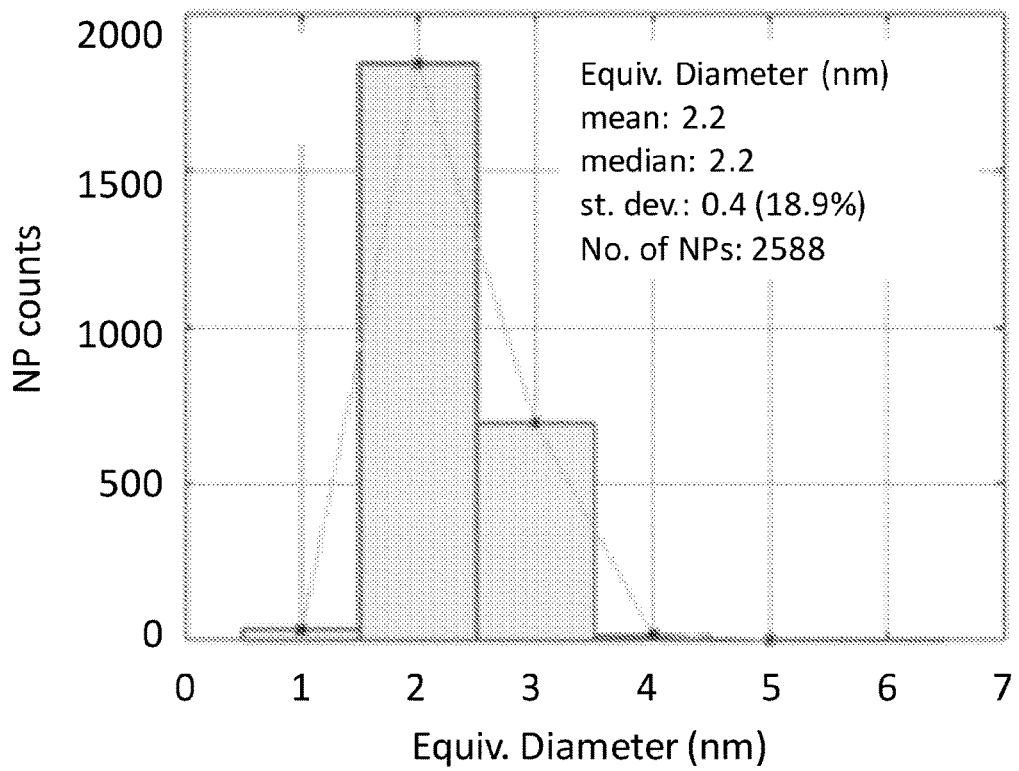
FIG. 7D: Core size distribution of 2-ethylhexaethiol-capped Au NPs having a narrow size distribution with an average diameter of about 2.2 nm.

The thiol-capped Au NPs dispersions were characterized using transmission electron microscopy (TEM). Samples for TEM were prepared by drop-casting 5:1 of diluted solution in toluene onto 200-mesh carbon-coated copper grids. TEM images (Model FEI Tecnai T12 G2 TEM) of the thiol-capped gold NPs were obtained at 120 kV. FIGS. 7A-7B show TEM images of thiol-caped Au NPs dispersion, including dodecanethiol-capped Au NPs dispersion (FIG. 7A) and 2-ethylhexaethiol-capped Au NPs dispersion (FIG. 7B). FIGS. 7C-7D show analysis of the metal core size distribution of thiol-caped Au NPs, including dodecanethiol-capped Au NPs (FIG. 7C) and 2-ethylhexaethiol-capped Au NPs (FIG. 7D). Transmission electron micrographs of the thiol-capped Au NPs confirmed the narrow size distribution of the dodecanethiol-capped Au NPs and of 2-ethylhexaethiol-capped Au NPs with a mean diameter of 2.4 nm and 2.2 nm, respectively.

Example 3: SiO$_2$ Micro-Barrier Preparation (Comparative Example)

An additional sensor device was prepared, containing a micro-barrier made of silicon oxide.

The SiO$_2$ micro-barrier was made using photolithography process at clean room facilities. A wafer comprising eight electrode arrays (as described in Example 1) was heated by a hot plate at 120° C. for 5 minutes. After the wafer was cooled down to room temperature then was coated with photoresist AZ 2070 by using a spinner (at 2000 rpm for 60 seconds). Then the wafer was heated by a hot plate at 110° C. for 2 minutes followed by UV light exposing through a special mask with intensity of 14 mW/cm2 for 4 sec. Then the photoresist was developed for 1 min using TMAH developer and washed with DI water. Depositing of SiO$_2$ was performed by standard plasma-enhanced chemical vapor deposition system (PECVD Plasma-Therm, Vision 410) under vacuum and then under silane (SiH$_4$) and oxygen atmosphere at 120° C. for 2 minutes. Then the wafer was placed in hot N-Methyl-2-pyrrolidone (NMP) for 2 hours followed by sonication in acetone for additional 30 minutes, followed by a lift-off process. The SiO$_2$ micro-barrier had a thickness of 100 μm, inner diameter of about 1000 μm and height of 2.4 μm.

Example 4: Micro-Barrier Characterization

Material surface characterization tests were conducted by an optical goniometer, (ramé-hart instrument co. model: 200-F1) an optical microscope integrated with a camera and scanning electron microscopy (SEM).

Surface images comprising a drop of water on the substrate surface, were captured in order to measure the static contact angle and the surface tension, thereby allowing to determine hydrophobicity of the surface. The contact angle is the angle in which the liquid interface meets the solid interface. The contact angle is determined by the balance between adhesive and cohesive forces. As the tendency of a drop to spread out over a flat, solid surface increases, the contact angle decreases. Thus, the contact angle provides an inverse measure of wettability. A high contact angle indicates a low wettability, in which the fluid minimizes the contact with the surface. Since the tested fluid is predominantly hydrophilic, a higher contact angle suggests a more hydrophobic surface.

Figure 8A:
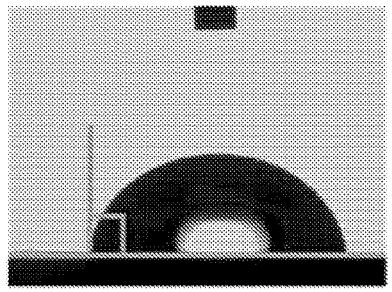
FIGS. 8A-8C. Optical microscopy images of contact angle at different micro-barriers.
Figure 8B:
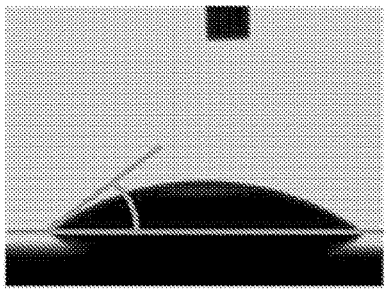
Figure 8C:
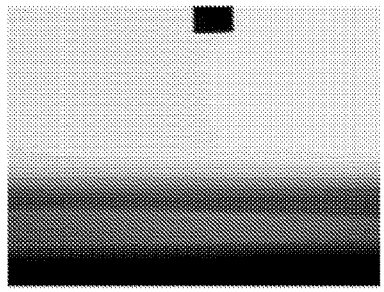

FIGS. 8A-8C show goniometer images of the contact angle at different micro-barrier surfaces, including image of SU-8 contact angle (FIG. 8A), image of oxygen-plasma treated SU-8 contact angle (FIG. 8B), and image of SiO$_2$ contact angle (FIG. 8C). The contact angles measured are 90±1° for SU-8 surface, 35±1° for treated SU-8 surface and no contact angle was formed at the SiO$_2$ surface. The untreated SU-8 is therefore a hydrophobic material.

Figure 9A:
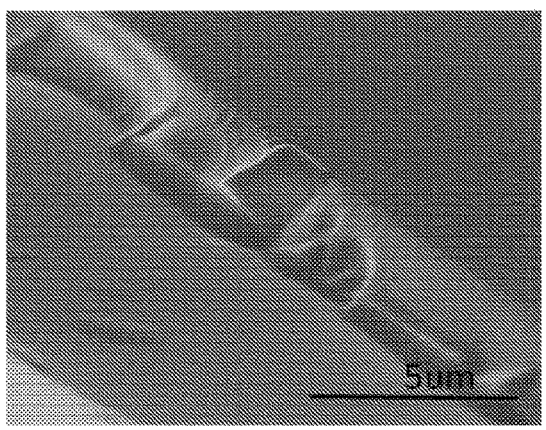
FIGS. 9A-9D. Scanning-electron microscopy (SEM) images of micro-barrier surface at different magnifications.
Figure 9B:
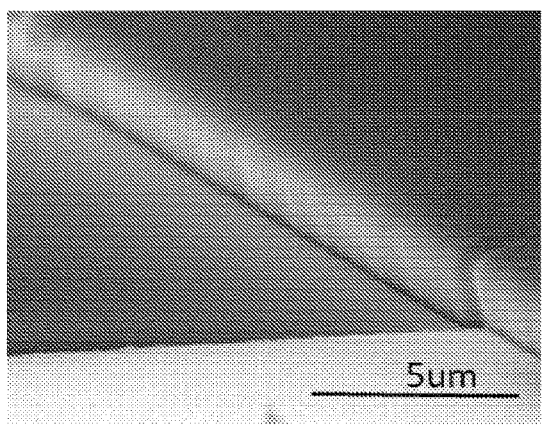
Figure 9C:
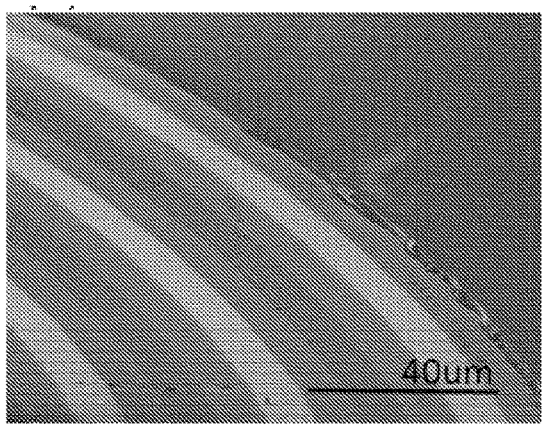
Figure 9D:
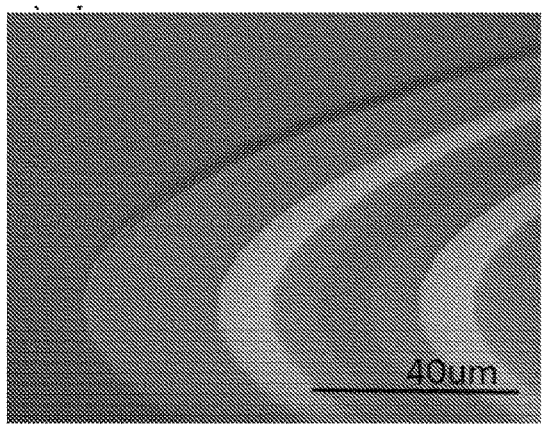
Figure 10A:
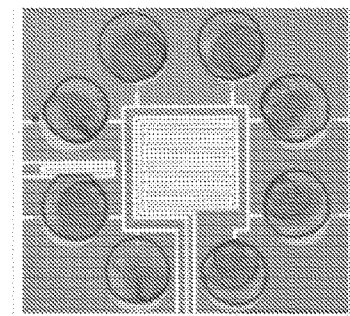
FIG. 10A: Light-microscopy image of a sensor comprising 8 electrode arrays and corresponding sensing layers prepared by deposition of 20 nL of 2-ethylhexaethiol-capped Au NPs dispersion.
Figure 10B:
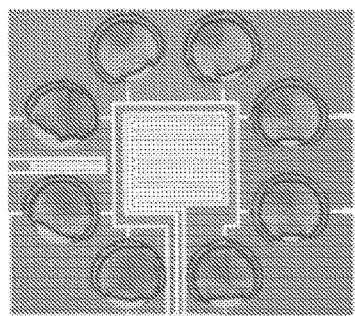
FIG. 10B: Light-microscopy image of a sensor comprising 8 electrode arrays and a sensing layer prepared by deposition of 20 nL of 2-ethylhexaethiol-capped Au NPs dispersion, wherein the sensing layer is confined by $SiO_2$ micro-barrier.
Figure 10C:
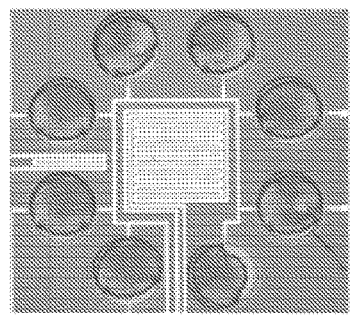
FIG. 10C: Light-microscopy image of a sensor comprising 8 electrode arrays and a sensing layer prepared by deposition of 20 nL of 2-ethylhexaethiol-capped Au NPs dispersion, wherein the sensing layer is confined by SU-8 micro-barrier.
Figure 10D:
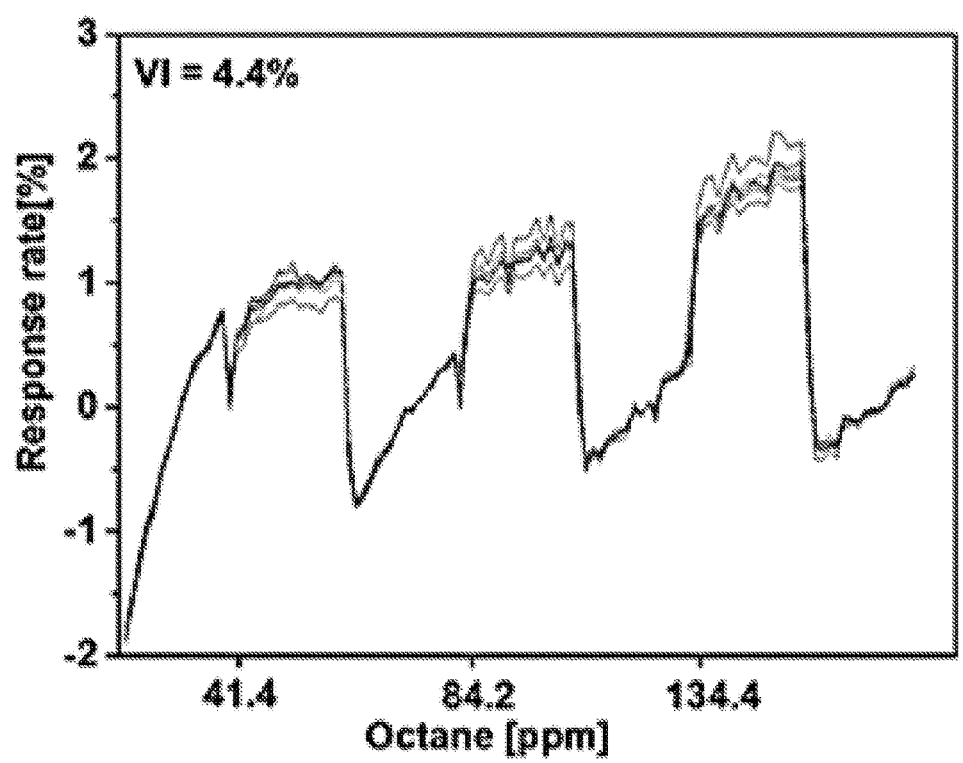
FIG. 10D: Response rate of a sensor to the exposure of different concentrations of n-octanol, wherein the sensor comprising 8 electrode arrays and a sensing layer prepared by deposition of 20 nL of 2-ethylhexaethiol-capped Au NPs dispersion.
Figure 10E:
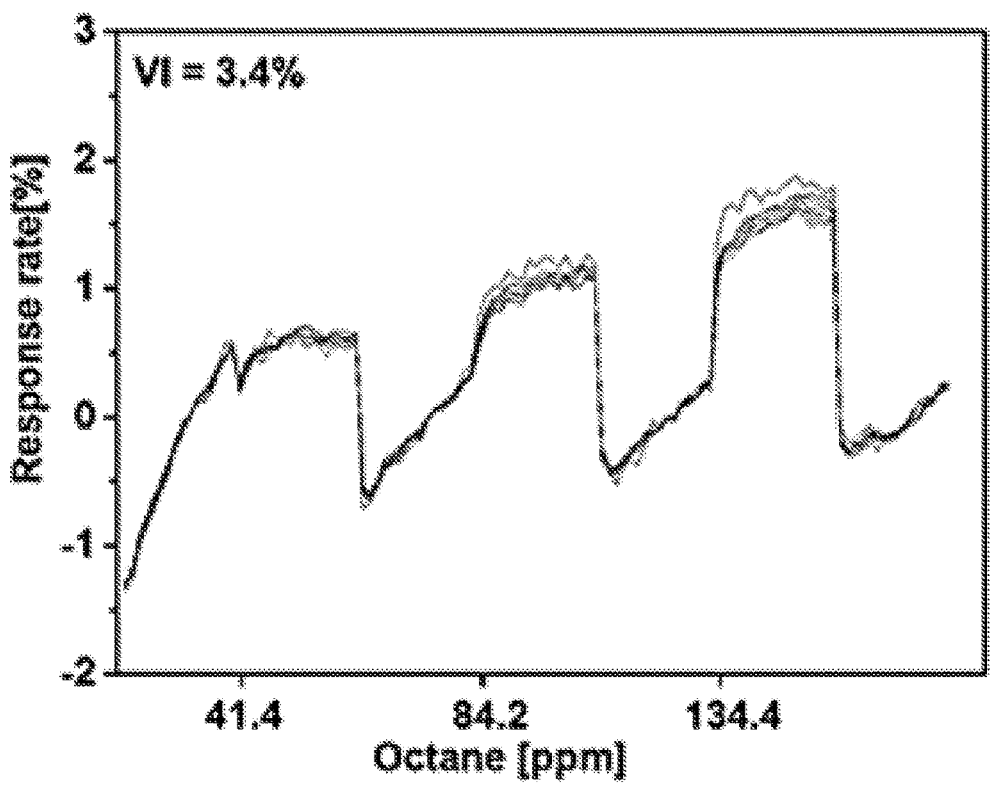
FIG. 10E: Response rate of a sensor to the exposure of different concentrations of n-octanol, wherein the sensor comprising 8 electrode arrays and a sensing layer prepared by deposition of 20 nL of 2-ethylhexaethiol-capped Au NPs dispersion, wherein the sensing layer is confined by $SiO_2$ micro-barrier.
Figure 10F:
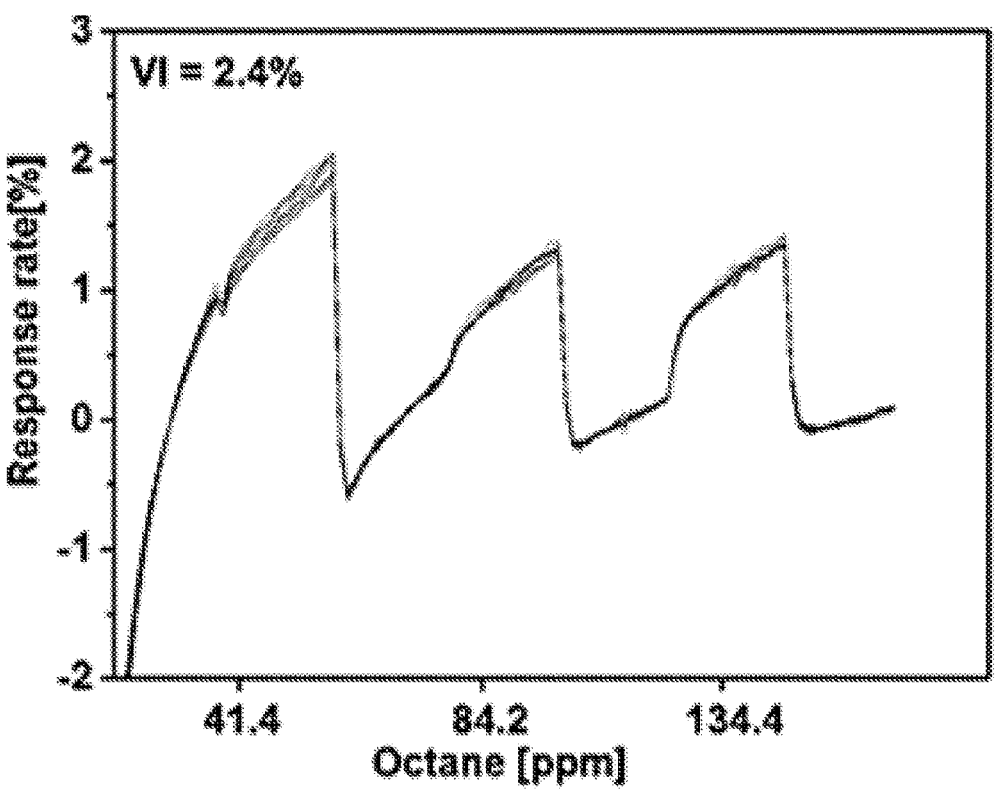
FIG. 10F: Response rate of a sensor to the exposure of different concentrations of n-octanol, wherein the sensor comprising 8 electrode arrays and a sensing layer prepared by deposition of 20 nL of 2-ethylhexaethiol-capped Au NPs dispersion, wherein the sensing layer is confined by SU-8 micro-barrier.
Figure 11E:
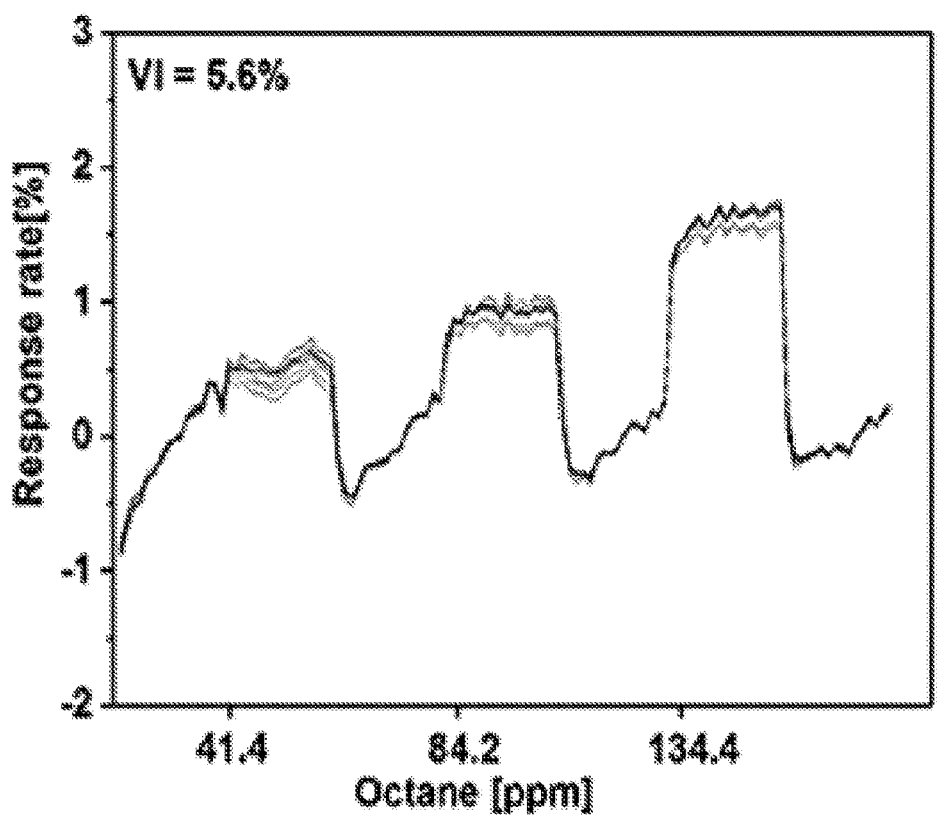
FIG. 11E: Response rate of a sensor to the exposure of different concentrations of n-octanol, wherein the sensor comprising 8 electrode arrays and a sensing layer prepared by deposition of 40 nL of 2-ethylhexaethiol-capped Au NPs dispersion, wherein the sensing layer is confined by $SiO_2$ micro-barrier.
Figure 11F:
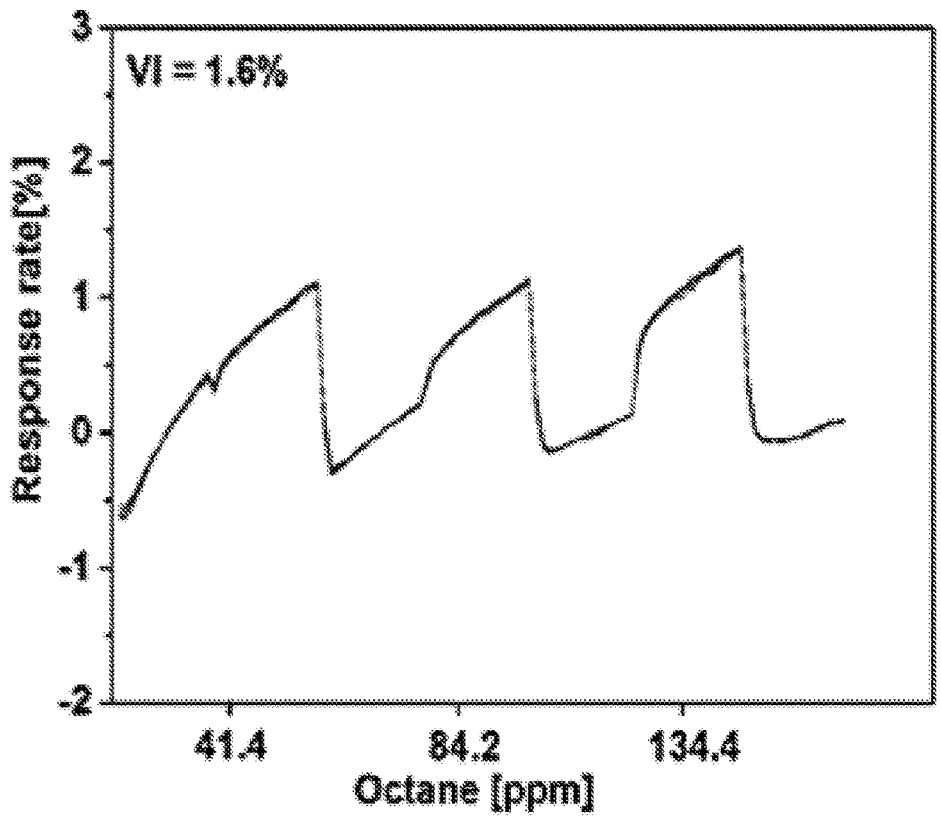
FIG. 11F: Response rate of a sensor to the exposure of different concentrations of n-octanol, wherein the sensor comprising 8 electrode arrays and a sensing layer prepared by deposition of 40 nL of 2-ethylhexaethiol-capped Au NPs dispersion, wherein the sensing layer is confined by SU-8 micro-barrier.

Additional SEM images were captured in order to study the morphology of micro-barrier surfaces. FIGS. 9A-9D show SEM images of the SU-8 and SiO$_2$ micro-barrier surfaces at different magnifications, including image of SiO$_2$ at 10k magnification (FIG. 9A), image of SU-8 at 10k magnification (FIG. 9B), image of SiO$_2$ at 1k magnification (FIG. 9C), and image of SU-8 at 1k magnification (FIG. 9D). SEM images of SiO$_2$ micro-barrier show wrecked edges and uneven and rough surface; which might result from the lift-off step during the preparation of the SiO$_2$ micro-barrier (Example 3). In contrast, the SEM images of SU-8 micro-barrier show straight edges and smooth surface.

Example 5: Sensor Characterization 12 different types of sensors were fabricated as detailed hereinabove in Examples 1 and 3. The sensors differed in organic ligand type (dodecanethiol and 2-ethylhexantiol), micro-barrier material (SU-8 and SiO$_2$), micro-barrier height (2.4, 5.5, and 17 μm) and deposited volume of the dispersion (20, 40, and 120 nL). At least 8 similar sensors were tested for each experimental parameter to evaluate the reproducibility of sensors' responses and morphology. Additionally, the effect of the addition of the micro-barrier was evaluated by comparing said sensors to sensors, which do not include any type of a micro-barrier.

The effect of the micro-barrier material and the volume of the dispersion were determined by analyzing morphology and measuring sensors' response to n-octane. Sensor response characterization results are summarized in Table 1.

Characterization of the sensing layer shape and morphology was performed by using light microscopy morphology pictures (FIGS. 10A-10C, 11A-11C, 12A-12C, and 13A-13C).

The response of the sensors to VOCs adsorption was measured as follows. The fabricated sensors were mounted on a custom polytetrafluoroethylene PTFE circuit board inside a stainless-steel test chamber with a volume of 100 cm$^2$. Exposure to the VOCs was preceded by an initial evacuation step, in which the sensors were placed in vacuum oven for 25 hours (2-ethylhexaethiol-capped Au NPs) or 45 hours (dodecanethiol-capped Au NPs). The electric signal (i.e., resistance as a function of time) produced by the sensors in response to the exposure to the VOCs was measured by a Keithley data-logger device (model 2701 DMM) controlled by a custom Labview program as function of time. A typical exposure cycle involved a 5 min vacuum (40 mtorr) baseline step, followed by 5 min under VOC exposure, and ended under vacuum for another 5 min. The sensors were exposed to n-Octane (CAS No. 11-65-9) at four different concentrations: 0, 41.4, 84.2 and 134.4 ppm.

A parameter which was used to evaluate the sensors detection ability was the amplitude (or response rate %), which indicates sensor signal amplitude at different analyte concentrations. Response rate can be calculated by Equation 1:

$$\Delta R/R_b * 100 \qquad \text{Equation 1}$$

where $\Delta R$ is the baseline-corrected steady-state resistance change upon exposure of the sensor to analyte and $R_b$ is the baseline resistance of the sensor in the absence of analyte.

FIGS. 10D-10F, 11D-11F, 12D-12F, and 13D-13F show the response rate % at four different concentrations of n-octane.

In order to evaluate reproducibility of the sensors' responses, average response (AVG) and standard deviation (STDEV) were calculated by comparing response changes at different conditions using MATLAB program. For each sensor the variability index (VI) was calculated (Equation 2). Low VI values indicate small distribution of the sensors' responses (i.e., high reproducibility).

$$VI = AVG\left(\frac{STDEV\frac{\Delta R}{R_{End}}}{AVG\frac{\Delta R}{R_{End}}}\right) \qquad \text{Equation 2}$$

where $R_{end}$ is relative resistance value at the end of response.

Example 6: Effect of the Micro-Barrier Material and Organic Ligand Type

FIGS. 10A-10F and 11A-11F compare the response of the three different sensor devices to n-octane, including a sensor without a micro-barrier, a sensor with SU-8 micro-barrier and a sensor with SiO$_2$ micro-barrier. Each device contained 8 individual sensors which were drop casted simultaneously and have the same structural and compositional characteristics. Additionally, two different volumes of the core-shell particles dispersion, including 20 nl (FIGS. 10A-10F) and 40 nl (FIGS. 11A-11F) were used to find the optimal casting volume. As can be seen from FIG. 10A, when using 20 nl of gold NPs modified with the organic ligand 2-ethylhexanthiol without a micro-barrier, the drop is not uniform and tends to flow outside the electrode array (FIG. 15A). The addition of a micro-barrier made of Si)$_2$ (FIG. 10B) restricts the flow of the deposited drop in an efficient manner. Yet, the sensing layers still adopt different uneven morphological shapes. Conversely, when the micro-barrier was made of SU-8, the casted sensors were contained within the micro-barrier, while adopting a more uniform structure. Functionally, when the uniformity of response of said sensors to different doses of octane was compared, it was found that the addition of the micro-barrier made of SU-8 provides higher increase in the reproducibility of sensor response (Table 1 and FIGS. 10C-10F).

TABLE 1

Sensing layer uniformity and sensor variability index (%).

| Dispersion of the core-shell particles | Deposited volume | VI (%) | | |
| --- | --- | --- | --- | --- |
| | | No barrier | SiO$_2$ barrier | SU-8 barrier |
| 2-ethylhexantiol capped Au NPs in toluene (20 mg/mL) | 20 nL | 4.4% | 3.4% | 2.45% |
| | 40 nL | 15.2% | 14.2% | 9.2% |
| dodecanethiol capped Au NPs in toluene (5 mg/mL) | 20 nL | 7.8% | 5.6% | 1.6% |
| | 40 nL | 12.6% | 12.9% | 2.5% |

It is therefore postulated that the solvent evaporation process on SU-8 surface was be the most moderate and uniform, leading to the most uniformly deposited MNPs films. The morphology of the sensing layers obtained with different micro-barrier materials further correlates with morphology studies of the SU-8 and the SiO$_2$ materials, showing a clear advantage of the SU-8 material which allows fabrication of a micro-barrier having a smooth surface.

In order to distinguish between the effect of the micro-barrier and a mere volume effect, the casted dispersion volume was increased from 20 nL to 40 nL. However, the results were similar to those obtained with 20 nL. The addition of a micro-barrier made from SiO2 helped to partially restrict the drop area, while the addition of a micro-barrier made of SU-8 polymer, restricts the drop more efficiently and reduced the morphology irregularity of the resulting sensors. The lowest VI value was obtained with the micro-barrier made from SU-8 (Table 1 and FIGS. 11C-11F).

Figure 12E:
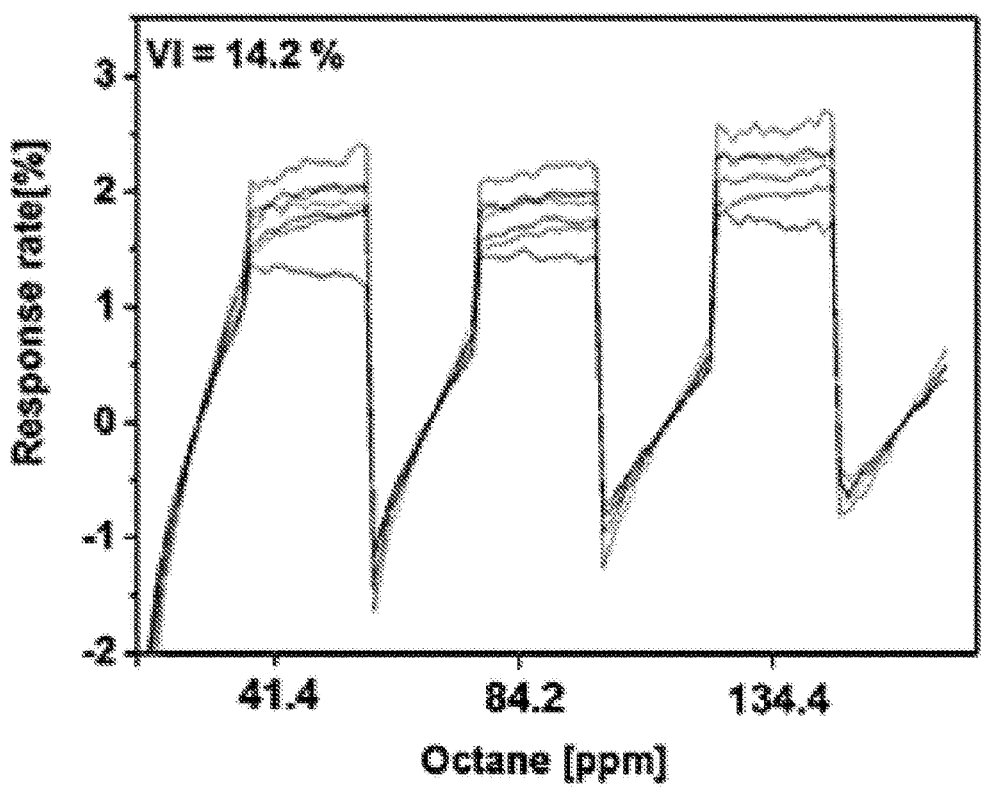
FIG. 12E: Response rate of a sensor to the exposure of different concentrations of n-octanol, wherein the sensor comprising 8 electrode arrays and a sensing layer made of 20 nL of dodecanethiol-capped Au NPs dispersion, wherein the sensing layer is confined by $SiO_2$ micro-barrier.
Figure 12F:
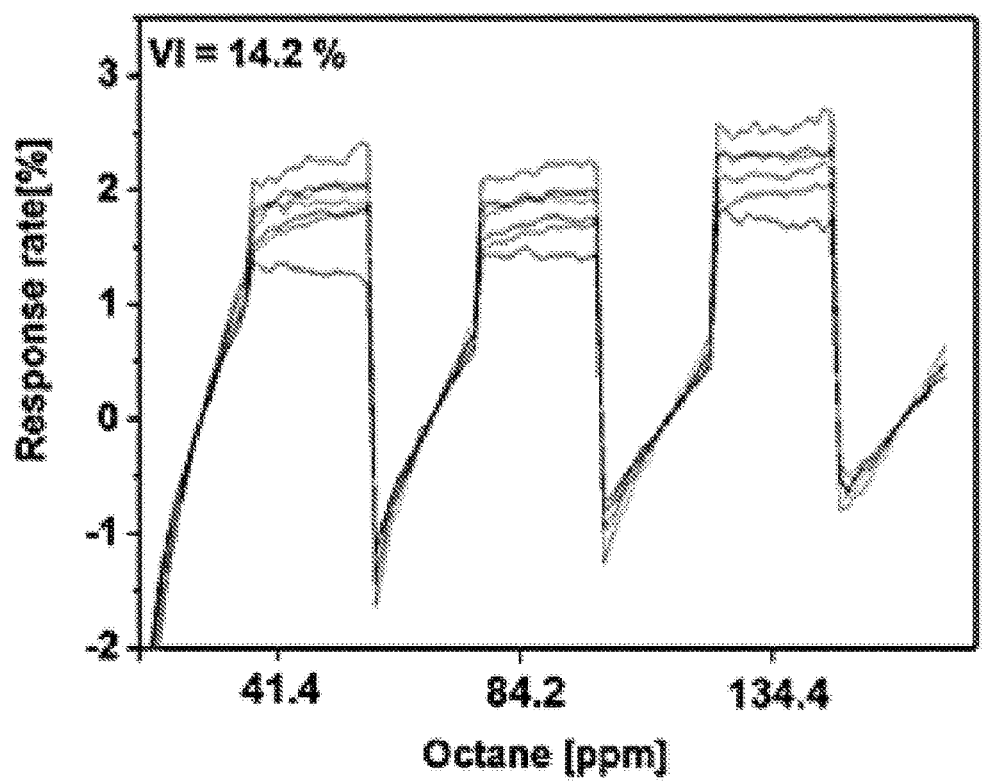
FIG. 12F: Response rate of a sensor to the exposure of different concentrations of n-octanol, wherein the sensor comprising 8 electrode arrays and a sensing layer prepared by deposition of 20 nL of dodecanethiol-capped Au NPs dispersion, wherein the sensing layer is confined by SU-8 micro-barrier.

In order to verify that these observations are not a unique case of a specific organic ligand, an additional organic ligand was chosen to functionalize gold NPs and the characterization tests were repeated. FIGS. 12A-12C show the sensing layer morphology when drop-casting 20 nL of dodecanethiol-based dispersion instead of 2-ethylhexantiol. Similar trend to that observed with the 2-ethylhexanethiol-based dispersion was observed for the three different manufacturing variants: without barrier, micro-barrier made of SiO$_2$, and SU-8 polymer, respectively. The VI also followed the same trend, going from 15.2% to 9.2% in the case of the micro-barrier made of SU-8 (Table 1 and FIGS. 12C-12F).

Figure 13E:
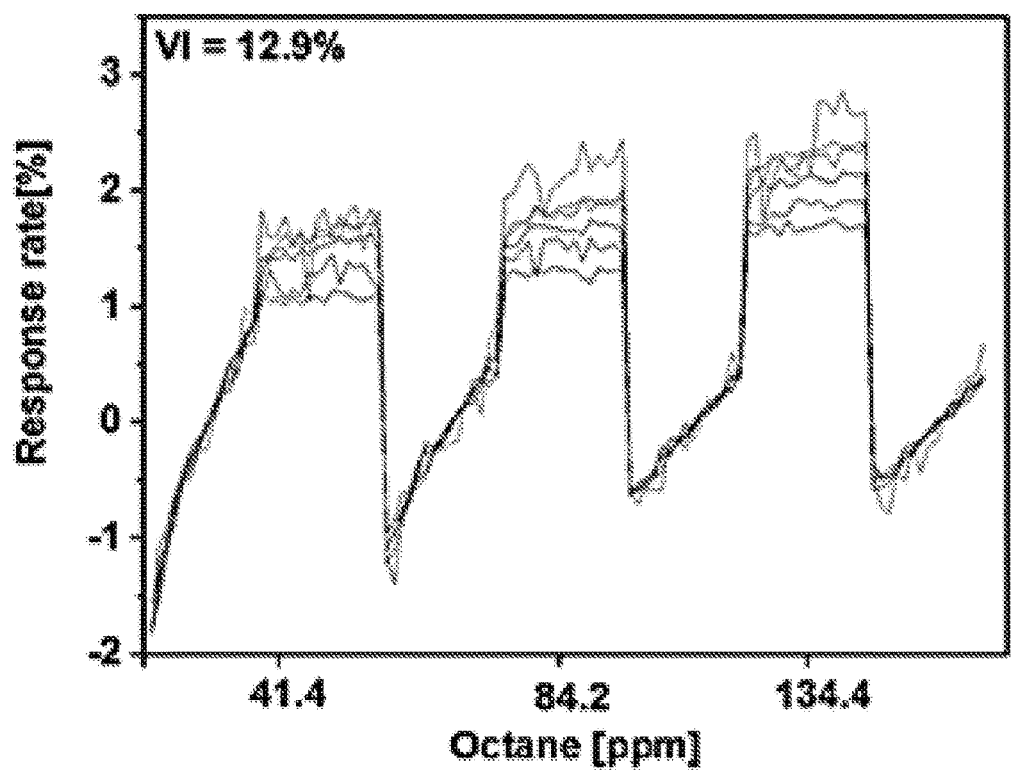
FIG. 13E: Response rate of a sensor to the exposure of different concentrations of n-octanol, wherein the sensor comprising 8 electrode arrays and a sensing layer prepared by deposition of 40 nL of dodecanethiol-capped Au NPs dispersion, wherein the sensing layer is confined by $SiO_2$ micro-barrier
Figure 13F:
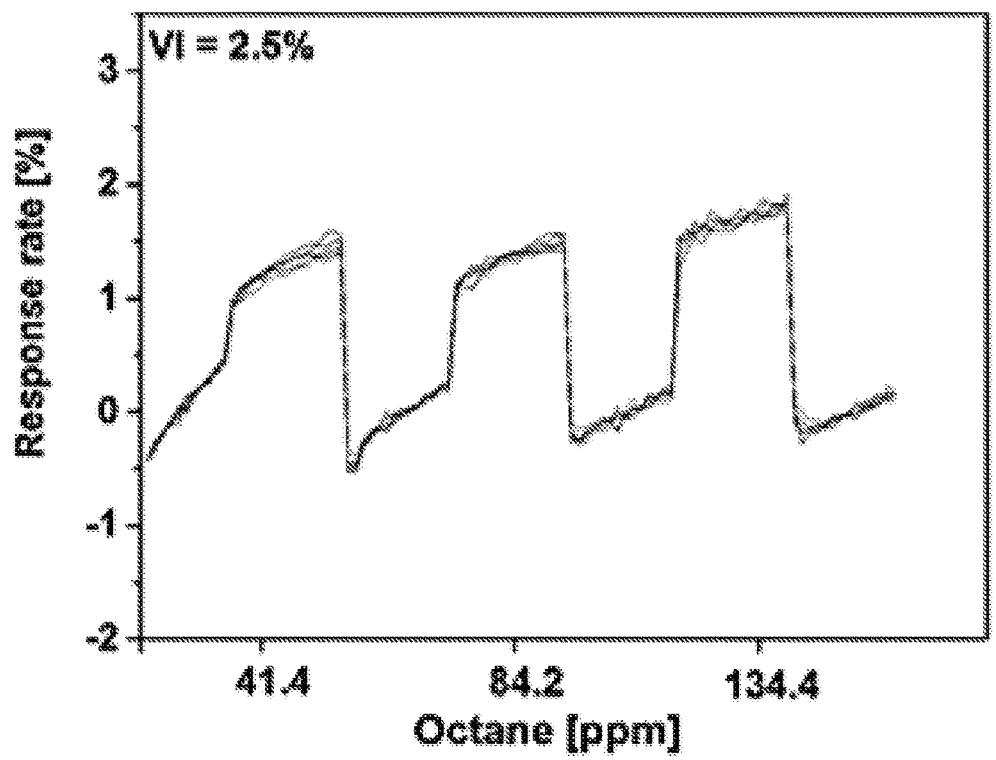
FIG. 13F: Response rate of a sensor to the exposure of different concentrations of n-octanol, wherein the sensor comprising 8 electrode arrays and a sensing layer prepared by deposition of 40 nL of dodecanethiol-capped Au NPs dispersion, wherein the sensing layer is confined by SU-8 micro-barrier.

FIGS. 13A-13C show morphology of the sensing layers obtained by drop casting 40 nL of a dispersion gold NPs modified with the organic ligand dodecanethiol. FIGS. 13D-13F show that the sensor response variance was again lowest when using the SU-8 micro-barrier, as VI decreased from 12.6% to 2.5% (Table 1).

It has therefore been shown that the addition of the micro-barrier increases morphological and functional uniformity of the sensors. Moreover, the fabrication of the micro-barrier from SU8, a hydrophobic material in nature, amplifies the effect of the micro-barrier addition and enables fabrication of devices that operate in a more uniform fashion.

Example 7: Optimization of the Drop Casted Volume and Micro-Barrier Height

It was shown that the uniformity of the sensors improves dramatically wherein the casting area around the electrodes is limited by a micro-barrier. The area of the casted drop was limited by a micro-barrier having a height of 2.35 µm. The micro-barrier thus forms a cavity, wherein the cavity is filled by the casted drop.

In order to evaluate the effect of the casted drop volume and finding the optimal casting volume, an experiment was performed, wherein varying dispersion volumes were applied onto the substrate and the electrodes with and without the micro-barrier, wherein the micro-barrier was made of SU-8 and its height was 2.35 µm. The casted dispersion was 5 mg/ml dodecanethiol in toluene. FIGS. 15A-15D schematically illustrate the height of the casted drop relatively to the micro-barrier (when present) depending on the volume of the applied dispersion. FIGS. 14A-14D show light-microscopy images of sensors comprising one electrode array and a sensing layer prepared by deposition of varying volumes of the 5 mg/mL dispersion of dodecanethiol-capped Au NPs in toluene. It can be seen from FIG. 14A that when preparing a sensing layer by depositing 15 nL of dodecanethiol-capped Au NPs dispersion without a micro-barrier, the obtained sensing layer was not uniform, as deposits of higher concentration of the NPs can be seen in the center and at the edges of the layer. FIG. 14B shows that when a micro-barrier was added and the volume of the deposition was reduced to 10 nL, the obtained sensing layer was still non-uniform at the edges and center thereof. FIG. 14C shows that when the micro-barrier was added and the volume of the deposited dispersion was increased to 22 nL, the obtained sensing layer had non-uniform edges. The most uniform sensing layer was obtained when the micro-barrier was added and the volume of the deposition was 20 nL (FIG. 14D).

It has therefore been shown that when the sensing layer is confined by a micro-barrier and the height of the casted-drop is essentially the same as the height of the micro-barrier (FIG. 15D) it increases the uniformity of the morphology of the sensing layer.

In another study the effect of different micro-barrier heights on sensor response uniformity was evaluated. Without wishing to being bound by theory or mechanism of action, it is assumed that the micro-barrier height can influence the formation of coffee rings, on the surface of the drying drop, which in turn can dictate an irregular behavior of sensors' responses. Three different SU-8 micro-barrier heights were tested, including 2.4, 5.5 and 17 µm. The volume of the deposited dispersion was also varied (20 nL, 40 nL, 120 nL, and 300 nL). Tables 2-3 summarize the results of the sensor unction characterization, including VI (Table 2) and response rate amplitude (Table 3).

As can be seen in Table 2, listing the VI of gold NP functionalized with the organic ligand 2-ethylhexanethiol, both 2.4 and 5.5 um micro-barrier heights displayed good VI of 1.3 and 1.6% respectively when the drop casted volume was 40 nL. However, the amplitude of these micro-barrier heights differed substantially (Table 3). The amplitude of the 40 nL drop casted on a micro-barrier of 2.4 u height was 0.31%, while the amplitude of the same volume drop casted on a 5.5 um ring amounted to 0.77%. This observation may be a chemistry specific phenomenon or may be a general trend. In order to distinguish between the two possibilities, this analysis was repeated with an additional functional group.

The second organic group was chosen again to be dodecanethiol. Table 2 further shows that 2.4 and 5.5 um micro-barrier heights provided similar VI of 2.5 and 2.6%, respectively. However, each barrier height works best with different drop casting volume. 40 nl works best for the 2.5 um barrier and 120 nl works best for the 5.5 um barrier. The amplitude showed a tradeoff between the two micro-barrier heights (Table 3).

TABLE 2 sensor variability index (%) with different micro-barrier heights.

| Barrier height | Casting solution | 20 nL | 40 nL | 120 nL | 300 nL |
|---|---|---|---|---|---|
| 2.4 µm | 2-ethylhexantiol capped Au NPs | 2.6% | 1.3% | 6.2% | NA |
|  | dodecanethiol capped Au NPs | 9.4% | 2.5% | 5.2% | NA |
| 5.5 µm | 2-ethylhexantiol capped Au NPs | 2.4% | 1.6% | 2.4% | 13.3% |
|  | dodecanethiol capped Au NPs | 9.7% | 21.4% | 2.6% | 5% |
| 17 µm | 2-ethylhexantiol capped Au NPs | 10.7% | 1.7% | 1.9% | 7.7% |
|  | dodecanethiol capped Au NPs | NA | NA | 39.7% | NA |

TABLE 3

Amplitude (%) of the sensors' responses with different micro-barrier heights.

| Barrier height |  | 20 nL | 40 nL | 120 nL | 300 nL |
|---|---|---|---|---|---|
| 2.4 µm | 2-ethylhexantiol capped Au NPs | 0.38% | 0.31% | 0.7% | NA |
|  | dodecanethiol capped Au NPs | 0.1% | 0.41% | 1.45% | NA |
| 5.5 µm | 2-ethylhexantiol capped Au NPs | 0.69% | 0.77% | 0.45% | 0.75% |
|  | dodecanethiol capped Au NPs | 0.2% | 0.4% | 1.14% | 1.29% |
| 17 µm | 2-ethylhexantiol capped Au NPs | 0.74% | 0.86% | 0.26% | 0.72% |
|  | dodecanethiol capped Au NPs | NA | NA | 0.92% | NA |

It is appreciated by persons skilled in the art that the present invention is not limited by what has been particularly shown and described hereinabove. Rather the scope of the present invention includes both combinations and sub-combinations of various features described hereinabove as well as variations and modifications. Therefore, the invention is not to be constructed as restricted to the particularly described embodiments, and the scope and concept of the invention will be more readily understood by references to the claims, which follow.

The invention claimed is:

1. A chemically sensitive sensor for detecting volatile organic compounds (VOCs), the sensor comprising:
    a substantially planar substrate having a top surface and a bottom surface, the substrate made of an electrically insulating material;
    an electrode array being disposed on the top surface of said substrate;
    a micro-barrier comprising an inner face and an outer face and being disposed on the top surface of the substrate and surrounding the electrode array; and
    a sensing layer comprising a multiplicity of core-shell particles in close-packed orientation, wherein said core-shell particles are arranged in a film configuration and said sensing layer is essentially devoid of a polymer, the particles comprising a metal nanoparticle (MNP) core and an organic ligand shell, wherein the MNP core has a mean particle size below about 15 nm, the sensing layer is in electric contact with said electrode array, and the shape of said sensing layer is confined by the micro-barrier.

2. The chemically sensitive sensor according to claim 1, wherein said micro-barrier is made of a hydrophobic material and wherein the sensing layer is hydrophobic.

3. The chemically sensitive sensor according to claim 1, wherein the micro-barrier has a cross-sectional shape selected from the group consisting of circular, oval, square, rectangular, triangular, hexagonal, and polygon shape.

4. The chemically sensitive sensor according to claim 1, wherein said micro-barrier has a height ranging from about 1 µm to about 20 um, a thickness ranging from about 10 µm to about 500 µm, and/or an inner perimeter ranging from about 0.2 mm to about 15 mm.

5. The chemically sensitive sensor according to claim 1, wherein said micro-barrier has a circular cross-sectional shape with an inner diameter ranging from about 0.2 mm to about 5 mm.

6. The chemically sensitive sensor according to claim 1, wherein the inner face of the micro-barrier is substantially smooth and substantially orthogonal to the top surface of the substrate.

7. The chemically sensitive sensor according to claim 1, wherein said micro-barrier is made of an epoxy-based photoresist.

8. The chemically sensitive sensor according to claim 1, wherein said MNP core has a mean particle size ranging from about 1.5 nm to about 5 nm.

9. The chemically sensitive sensor according to claim 1, wherein the organic ligand shell has a thickness ranging from about 1.2 nm to about 7 nm.

10. The chemically sensitive sensor according to claim 1, wherein the MNP core comprises a metal selected from the group consisting of Au, Pt, Ag, Ni, Co, Pd, Cu, Al, Zn, Fe, and combinations thereof or a metal alloy selected from the group consisting of Au/Pt, Au/Ag, Au/Cu, Au/Ag/Cu, Au/Pd, Au/Ag/Cu/Pd, Pt/Rh, Ni/Co, and Pt/Ni/Fe.

11. The chemically sensitive sensor according to claim 10, wherein the MNP core comprises Au.

12. The chemically sensitive sensor according to claim 1, wherein said organic ligand is selected from the group consisting of alkylthiols, arylthiols, alkylarylthiols, alkylthiolates, ω-functionalized alkanethiolates, arenethiolates, (γ-mercaptopropyl) tri-methyloxysilane, dialkyl disulfides, and combinations and derivatives thereof.

13. The chemically sensitive sensor according to claim 12, wherein the ligand is selected from the group consisting of dodecanethiol, 2-ethylhexanethiol, decanethiol, hexanethiol, dibutyl disulfide, 4-tert methylbenzenethiol, 1-heptanethiol, butanethiol, benzylmercaptan, 3-ethoxytiophenol, tert-dodecanethiol, and combinations thereof.

14. The chemically sensitive sensor according to claim 1, wherein the sensing layer has a substantially uniform thickness throughout its entire area.

15. The chemically sensitive sensor according to claim 1, wherein the substrate is made of the electrically insulating material selected from the group consisting of silicon, silicon dioxide, quartz, glass, ceramic, plastic, Teflon, Kapton, and combinations thereof, and/or the electrodes are made of a material selected from the group consisting of Au, Pt, Ti, Cu, Ag, Pd, Ni, Al, and alloys and combinations thereof.

16. A method for fabricating a chemically sensitive sensor for detecting VOCs, the method comprising the steps of:
  i) providing a substantially planar substrate having a top surface and a bottom surface, the substrate being made of an electrically insulating material;
  ii) forming an electrode array on the top surface of the substrate;
  iii) forming a micro-barrier on the top surface of the substrate, wherein the micro-barrier surrounds the electrode array; and
  iv) forming a sensing layer comprising a multiplicity of core-shell particles in close-packed orientation by applying a dispersion comprising the core-shell particles and a solvent onto the top surface of the substrate and/or the electrode array within the micro-barrier, wherein said dispersion is applied in a volume which forms a drop, having essentially the same height as the height of the micro-barrier, the particles comprising a metal nanoparticle (MNP) core and an organic ligand shell, wherein the MNP core has a mean particle size below about 15 nm, the sensing layer is in electric contact with the electrode array, and the shape of the sensing layer is confined by said micro-barrier.

17. The method according to claim 16, wherein the step of forming the micro barrier is performed by a photolithography process comprising applying a negative photoresist to the substrate and the electrode array, disposing a mask with a predefined pattern on the negative photoresist, exposing the negative photoresist to UV irradiation, and developing the remaining negative photoresist.

18. A method for fabricating a chemically sensitive sensor for detecting VOCs, the method comprising the steps of:
  i) providing a substantially planar substrate having a top surface and a bottom surface, the substrate being made of an electrically insulating material;
  ii) forming an electrode array on the top surface of the substrate;
  iii) forming a micro-barrier on the top surface of the substrate, wherein the micro-barrier surrounds the electrode array; and
  iv) forming a sensing layer comprising a multiplicity of core-shell particles in close-packed orientation by applying a hydrophobic dispersion comprising the core-shell particles and a solvent onto the top surface of the substrate and/or the electrode array within the micro-barrier, wherein said dispersion is applied in a volume which forms a drop, having essentially same height as the height of the micro-barrier, the particles comprising a metal nanoparticle (MNP) core and an organic ligand shell, wherein the MNP core has a mean particle size below about 15 nm, the sensing layer is in electric contact with the electrode array, and the shape of the sensing layer is confined by said micro-barrier.

19. The method according to claim 18, wherein the dispersion is applied by a process selected from inkjet-printing and drop-casting.

* * * * *